(12) United States Patent
Everman et al.

(10) Patent No.: US 11,950,909 B2
(45) Date of Patent: Apr. 9, 2024

(54) APPARATUSES AND METHODS FOR INDIVIDUALIZED POLYGRAPH TESTING

(71) Applicant: GMECI, LLC, Beavercreek, OH (US)

(72) Inventors: Bradford R Everman, Haddonfield, NJ (US); Brian Bradke, Brookfield, VT (US)

(*) Notice: Subject to any disclaimer, the term of this patent is extended or adjusted under 35 U.S.C. 154(b) by 0 days.

(21) Appl. No.: 18/072,397

(22) Filed: Nov. 30, 2022

(65) Prior Publication Data

US 2023/0109763 A1    Apr. 13, 2023

Related U.S. Application Data

(63) Continuation-in-part of application No. 17/387,491, filed on Jul. 28, 2021, now Pat. No. 11,604,513.

(51) Int. Cl.
| | |
|---|---|
| *A61B 5/16* | (2006.01) |
| *A61B 5/00* | (2006.01) |
| *A61B 5/024* | (2006.01) |

(52) U.S. Cl.
CPC .......... *A61B 5/164* (2013.01); *A61B 5/02416* (2013.01); *A61B 5/7221* (2013.01);
(Continued)

(58) Field of Classification Search
CPC ......... A61B 5/164; A61B 5/7267; A61B 5/16; A61B 5/7221; A61B 5/7246; A61B 5/097;
(Continued)

(56) References Cited

U.S. PATENT DOCUMENTS

| | | | |
|---|---|---|---|
| 5,447,166 A | * 9/1995 | Gevins | .............. A61B 5/377 |
| | | | 128/925 |
| 7,138,905 B2 | 11/2006 | Pavlidis | |

(Continued)

FOREIGN PATENT DOCUMENTS

AU    2021102773 A4 * 3/2022

OTHER PUBLICATIONS

Wang, Detecting concealed information using functional near-infrared spectroscopy (fNIRS) combined with skin conductance, heart rate, and behavioral measures, (journal), Feb. 22, 2022, Psychophysiology, vol. 59, Issue 8, Article: e14029, Aug. 2022, p. 1-14.

(Continued)

*Primary Examiner* — Xuemei Zheng
(74) *Attorney, Agent, or Firm* — Caldwell Intellectual Property Law

(57) ABSTRACT

Aspects relate to apparatuses and methods for individualized polygraph testing. The apparatus including at least an interface configured to communicate questions to the user, at least a sensor configured to detect biofeedback signals as a function of a biofeedback of a user, wherein the biofeedback is associated with at least an answer to at least a question, and at least a computing device including at least a processor and a memory communicatively connected to the at least a processor, the memory containing instructions configuring the at least a processor to receive the biofeedback signals, generate a user state classifier, train the user state classifier as a function of a user state training set, wherein the user state training set includes biofeedback signals correlated to answers of known veracity, and classifying a biofeedback signal of the biofeedback signals to a user state as a function of the user state classifier.

18 Claims, 13 Drawing Sheets

(52) U.S. Cl.
CPC .......... *A61B 5/7246* (2013.01); *A61B 5/7267* (2013.01); *A61B 5/7405* (2013.01); *A61B 5/742* (2013.01)

(58) Field of Classification Search
CPC ........... A61B 5/087; A61B 5/06; A61B 5/024; A61B 5/02416; A61B 5/02405; A61B 5/02438; A61B 5/162; A61B 5/72; A61B 5/7235; A61B 5/7264; A61B 5/742; A61B 5/7425; A61B 5/743; A61B 5/7405; G09B 5/06

See application file for complete search history.

(56) References Cited

U.S. PATENT DOCUMENTS

| | | |
|---|---|---|
| 10,702,154 B2 | 7/2020 | Porges |
| 2016/0203726 A1* | 7/2016 | Hibbs .................... A61B 5/165 434/308 |
| 2018/0160959 A1* | 6/2018 | Wilde .................... G06N 20/00 |
| 2018/0307362 A1 | 10/2018 | Komala et al. |
| 2019/0033914 A1 | 1/2019 | Aimone et al. |
| 2019/0167211 A1 | 6/2019 | Everman et al. |
| 2020/0383621 A1 | 12/2020 | Cuestas |
| 2021/0096646 A1 | 4/2021 | Yildiz et al. |
| 2021/0386343 A1* | 12/2021 | Goldenberg ......... A61B 5/1032 |
| 2021/0398562 A1 | 12/2021 | Verbeke et al. |
| 2022/0087584 A1 | 3/2022 | Kircher |

OTHER PUBLICATIONS

Gurel, Fusing Near-Infrared Spectroscopy With Wearable Hemodynamic Measurements Improves Classification of Mental Stress, (journal), IEEE Sensors Journal, vol. 19, Issue: 19, p. 8522-8531, IEEE.

\* cited by examiner

APPARATUSES AND METHODS FOR INDIVIDUALIZED POLYGRAPH TESTING

CROSS-REFERENCE TO RELATED APPLICATIONS

This application is a continuation-in-part of Non-provisional application Ser. No. 17/387,491 filed on Jul. 28, 2021 and entitled "METHODS AND SYSTEMS FOR INDIVIDUALIZED CONTENT MEDIA DELIVERY," the entirety of which is incorporated herein by reference.

FIELD OF THE INVENTION

The present invention generally relates to the field of polygraph testing. In particular, the present invention is directed to Apparatuses and methods for individualized polygraph testing.

BACKGROUND

Current methods of polygraph testing are insufficient. There is a need for individualized testing methods that more accurately assess a person's veracity.

SUMMARY OF THE DISCLOSURE

In an aspect apparatus for individualized polygraph testing. The apparatus including at least an interface configured to communicate questions to the user, at least a sensor configured to detect biofeedback signals as a function of a biofeedback of a user, wherein the biofeedback is associated with at least an answer to at least a question, and at least a computing device including at least a processor and a memory communicatively connected to the at least a processor, the memory containing instructions configuring the at least a processor to receive the biofeedback signals, generate a user state classifier, train the user state classifier as a function of a user state training set, wherein the user state training set includes biofeedback signals correlated to answers of known veracity, and classify at least a biofeedback signal of the biofeedback signals to a user state as a function of the user state classifier.

In another aspect a method for individualized polygraph testing The method including communicating, by at least an interface, questions to the user, detecting, by at least a sensor, biofeedback signals as a function of a biofeedback of a user, wherein the biofeedback is associated with at least an answer to at least a question, receiving, by a computing device, the biofeedback signals, generating, by the computing device, a user state classifier, training, by the computing device, the user state classifier as a function of a user state training set, wherein the user state training set comprises biofeedback signals correlated to answers of known veracity, and classifying, by the computing device, at least a biofeedback signal of the biofeedback signals to a user state as a function of the user state classifier.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for individualized content delivery. In an embodiment, apparatuses and methods described herein may allow for remote operation, automatic operations, non-interventional, easy implementation, and/or low-cost polygraph testing.

Aspects of the present disclosure allow for individualized polygraph testing without the need of an expert or additional third party. Exemplary embodiments illustrating aspects of the present disclosure are described below in the context of several specific examples.

Figure 1:
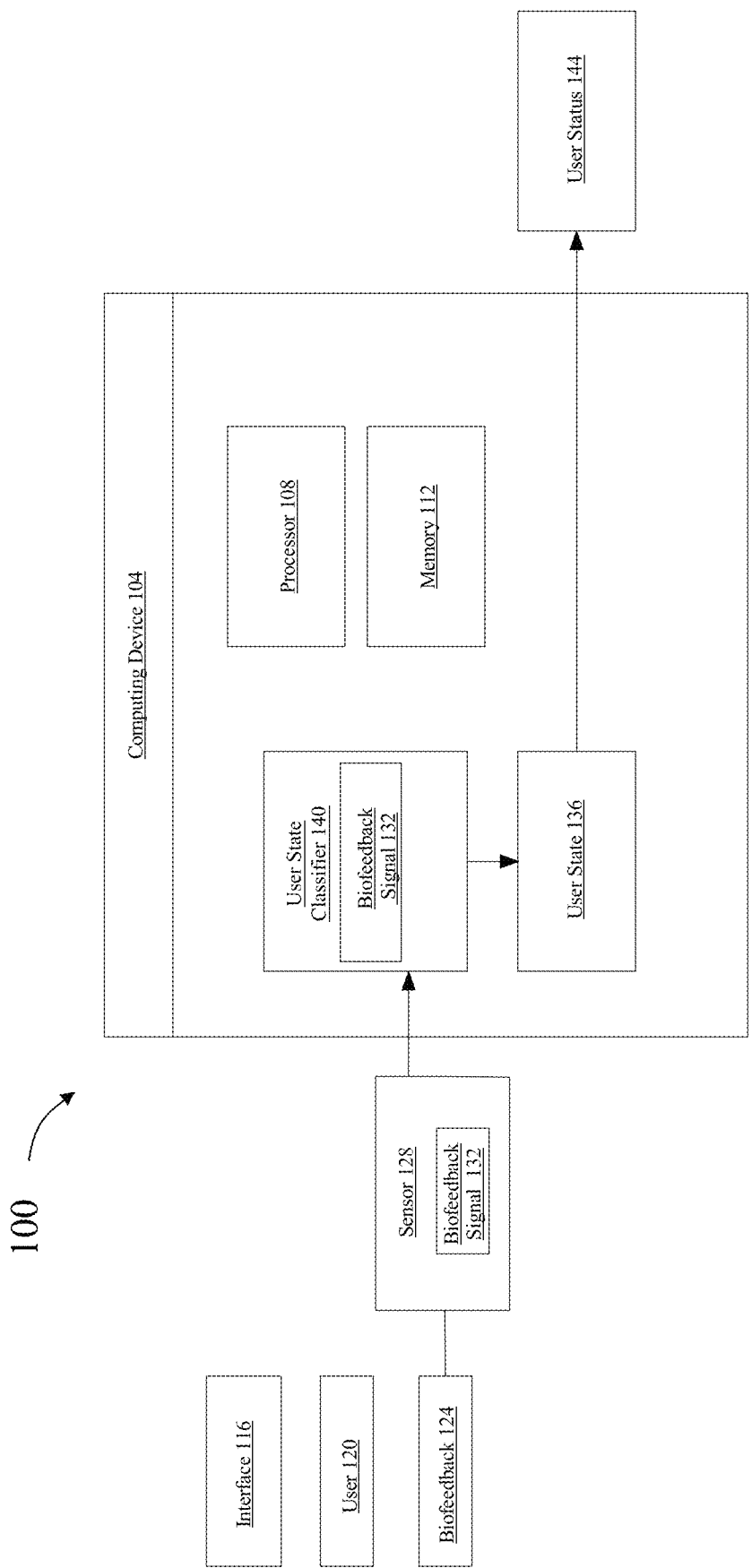
FIG. 1 is a block diagram illustrating a system for individualized polygraph testing.

Referring now to FIG. 1, an exemplary embodiment of an apparatus 100 for individualized polygraph testing is illustrated. A "polygraph test," used in this disclosure, is a test that includes a device configured to measure biological parameters of a person while that person is responding to a question. As used in the current disclosure, a "biological parameter" is datum describing a biological state of user 120. As used in the current disclosure, a "biological state" is a physical condition associated with the user 120. For example, a biological parameter may include the measurement of a person's heart rate, blood pressure, body temperature, serum levels of various stress hormones (e.g. cortisol) and immunological functions (e.g. suppression of lymphocyte activity), and the like.

Still referring to FIG. 1, apparatus 100 includes a computing device 104. Computing device 104 may include any computing device as described in this disclosure, including without limitation a microcontroller, microprocessor, digital signal processor (DSP) and/or system on a chip (SoC) as described in this disclosure. Computing device 104 includes a processor 108 and a memory 112 communicatively connected to the processor 108, wherein memory 112 contains instructions configuring processor 108 to carry out the generating process. As used in this disclosure, "communicatively connected" means connected by way of a connection, attachment, or linkage between two or more relate which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of apparatus 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 may include at least a sensor 128. As used in this disclosure, a "sensor" is any device that is configured to detect a parameter and transmit a signal according to the detected parameter. For instance, in some embodiments, a sensor 128 may be configured to detect a biofeedback 124 of a user 120. As used in this disclosure, "biofeedback," is biological parameter that is indicative of a response. Biofeedback 124 is associated with at least an answer to at least one question. An "answer," as used in this disclosure, expression from a user 120 in response to a question. An answer may be, as non-limiting examples, verbal, physical, and/or written. Biofeedback 124 may in some cases be a biological parameter that is indicative of a user 120's confidence. "Confidence," as used in this disclosure, is honesty. Biofeedback 124 may relate to detection of a biological parameter that occurs when a user 120 is being dishonest in an answer. For example, increased heart rate, excessive sweating, unfocused or sporadic eye movements, heavy breathing, irregular body movements, such as twitches and the like. In some cases, at least a sensor 128 may be configured to detect at least a biofeedback signal 132 as a function of a biofeedback 124 of a user 120 wherein the biofeedback 124 is associated with at least an answer to at least a question. As used in this disclosure, a "biofeedback signal" is at least an element of data associated with detection of biofeedback 124. As used in this disclosure, a "signal" is a representation of at least an element of data. A signal may include an analog signal, a digital signal, an electrical signal, an optical signal, and the like. In some cases, a signal may be represented according to one or more protocols, for example without limitation universal asynchronous receiver-transmitter (UART), serial communication protocols, parallel communication protocols, and/or Ethernet protocols.

In some cases, at least a sensor 128 may perform one or more signal processing steps on a biofeedback signal 132. For instance, sensor 128 may analyze, modify, and/or synthesize a biofeedback signal 132 in order to improve the signal, for instance by improving transmission, storage efficiency, and/or signal to noise ratio. Exemplary methods of signal processing may include analog, continuous time, discrete time, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits: sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point, floating-point, real-valued, and/or complex-valued multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal. In some cases, biofeedback 124 may be found (for instance through machine-learning processes described below) to correlate with certain levels of user present confidence. As used in this disclosure, "user present confidence" is the quality of a user's honesty. For a user's ability respond or act honestly to delivered question or a task unrelated to the delivered question. In some cases, user 120 present confidence may be quantitatively represented by way of a confidence metric. As used in this disclosure, a "confidence metric" is a measure of user 120's present confidence. Non-limiting examples of confidence metric include results on a test or quiz, quantified performance of a duty or job function, and/or achievement of certain physical and mental objectives. In some cases, one or more machine-learning processes in this disclosure may be calibrated and/or trained using confidence metrics, for example confidence metrics correlated to biofeedback 124, and/or display parameters for an individual user 120, a cohort of users 120, or a population of users 120.

With continued reference to FIG. 1, apparatus 100 includes at least an interface 116 configured to communicate question to user 120. Question may be related to content as defined further below. As used in this disclosure, an "interface", is an interconnection between a user and a system. Interface 116 may include a graphical user interface, command line interface (CLI), menu-driven user interface, touch user interface, voice user interface (VUI), form-based user interface, natural language user interface, and the like. For example, interface 116 may provide an interconnection between a user and a communication device, such as a computer screen, a television, radio, speaker, a projector and the like; in some cases, a display may comprise an audio-visual display and thereby may additionally include at least an audio transducer (e.g., speakers). Exemplary non-limiting displays include liquid crystal displays, cathode ray tube displays, light emitting diode displays, organic light emitting diode displays, quantum dot displays, micro-electromechanical system (MEMS) projector, virtual reality headset, head mounted display, and the like. In some embodiments, interface 116 may communicate content to user 120. As described in this disclosure, "content" is any media (e.g., visual and/or audio) which contains information intended to be communicated to an audience. Exemplary content includes course a document, slide show, spreadsheet, diagram, video, audio, images, interactive media, a question, text, and the like. A "question," as used in this disclosure, is an interrogative expression used to test veracity. For example, a question may be, as non-limiting examples, a verbal, written, typed, interrogative expression. Questions may be related to content presented to user 120 through interface 116. For example, a picture of a flowerpot may be communicated to user 120 through interface 116 along with a question asking user 120 if they recognize the flowerpot in the image. In some embodiments, questions may be related to one another may be communicated to user 120 without the aid of content. For example, "what is your name," "what is your address," "were you at this address on the night of September $4^{th}$," and the like. In some additional embodiments, apparatus 100 may be used with a live instructor (i.e., teacher, professor, trainer, supervisor, and the like), for example taking place of interface 116 or being presented by way of interface 116. In some cases, questions may be used for professional training, scholastic education, military training, physical training, satisfying one's curiosity, sport's training, self-help, therapy, meditation, mindfulness training, and the like. In some additional embodiments, questions may include material interacted with by a subject, for example in service of a job or task. As an example, questions may include security camera footage and a subject viewing the questions may include security personnel. In another non-limiting embodiment, questions may include interactive questions, for example a control interface 116 for an unmanned aerial vehicle (UAV) and subject interacting with the questions may include a UAV pilot. In some cases, questions may include a representation of a live environment, such as in the cases of the UAV pilot and the security personnel. Another such example is an application in which questions represents air traffic control communication and subject interacting with the questions is an air traffic controller. Questions may be delivered substantially with or without a display. For example, questions may be delivered through audio or through a live scene (e.g., live presenter).

Still referring to FIG. 1, in some embodiments, computing device 104 may additionally be configured to control at least a display parameter for at least a interface 116. As used in this disclosure, a "display parameter" is a controllable characteristic of a display. Exemplary non-limiting display parameters may include visual parameters, audio parameters, and/or content parameters. As used in this disclosure, "audio parameters" is a controllable sound characteristic. Exemplary non-limiting audio parameters may include audio volume, audio mixer settings (e.g., treble, mid, bass, etc.), audio balance settings (e.g., left, right, etc.), audio fade settings (e.g., front, back, etc.), audio content settings (e.g., white noise, pink noise, etc.), and the like. In some cases, an audio parameter may include at least a change to audio content. For example, in some cases content may be augmented with audio intended to have an effect on a state of a user 120; for instance, a precipitous and loud sound may be inserted in order to increase alertness of a user 120. In some cases, display parameter may include a speed of presentation of content and questions. For example, speed of presentation may be varied continuously and/or discretely from 0.5× to 3.0× speed of presentation. In some cases, a display parameter may include position of presentation of questions, for instance within the display. In some embodiments, questions may move within a display and according to a display parameter in response to biofeedback signal 132 and in order to improve a user 120's receptiveness to the questions. In some embodiments, speed of presentation may be controlled substantially proportional with a measured level of confidence of user 120, for example according to detected biofeedback 124. In some cases, computing device 104 may be configured to control at least a interface 116 as a function of a biofeedback signal 132. For instance computing device 104 may control at least a display parameter by generating a display machine-learning model as a function of a display machine-learning algorithm; training the display machine-learning model as a function of a display training set, wherein the display training set comprises biofeedback 124 inputs correlated to display parameter and/or confidence metric outputs; and generating the at least a display parameter as a function of the at least a biofeedback signal 132 and the display machine-learning model. As used in this disclosure, a "display machine learning-model" is a machine-learning model that takes as input at least a biofeedback 124 and outputs at least a display parameter. In some embodiments, the display training set may include biofeedback 124 and/or confidence metric inputs correlated to display parameter outputs. Display machine-learning model may include any machine-learning model described in this disclosure. As used in this disclosure, a "display machine-learning algorithm" is a machine-learning algorithm that is used to generate a display machine-learning model. Display machine-learning algorithm may include any machine-learning algorithm and/or process described in this disclosure. As used in this disclosure, a "display training set" is training data that is used to train display machine-learning model. According to some embodiments, display training set may include biofeedback 124 inputs correlated to display parameter outputs. Display training set may include any training set and/or training data described in this disclosure.

Still referring to FIG. 1, in some embodiments, computing device 104 may be additionally configured to classify a user state 136, for instance by using a user state classifier 140. As used in this disclosure, a "user state" is a classification of an answer received from a user 120. A classification of an answer may include honest, dishonest, intermediate, and the like. In some cases, the user state 136 may be classified according to a user 120 present confidence. For example, a user 120 present confidence may be related to a user's ability answer honestly per question, such as performance on a quiz on the communicated questions.

In some cases, a user 120 present confidence may be qualitatively and/or quantitatively determined according to other metrics, sensors 128, and/or measures. For example, a user's veracity in answering a question and used as an input in any machine-learning process described in this disclosure. Exemplary non-limiting user states 136 may include honest, dishonest, attentive, inattentive, focused, unfocused, and the like. Computing device 104 is configured to receive the biofeedback signals 132 from sensor 128. In some cases, computing device 104 may classify a user state 136 as a function of biofeedback signal 132. For instance, computing device may be configured to classify a user state 136 by generating a user state classifier 140 as a function of a user state 136 machine-learning algorithm; training the user state classifier 140 as a function of a user state 136 training set; and classifying the user state 136 as a function of the user state classifier 140 and the biofeedback signal 132. As used in this disclosure, a "user state classifier" is a classifier that takes as input at least a biofeedback 124 and outputs a user state 136. User state classifier 140 may include any machine-learning model and/or classifier described in this disclosure. As used in this disclosure, a "user state machine-learning algorithm" is a machine-learning algorithm that is used to generate a user state classifier 140. User state 136 machine-learning algorithm may include any machine-learning algorithm and/or process described in this disclosure. User state classifier 140 may take biofeedback 124, wherein biofeedback 124 may contains a plurality of parameters detected as a result of a user 120's response, both verbal and physical, to delivered questions. Each response from a user 120 correlated to a biological parameter may be classified to a user 120 present confidence represented a confidence metric. User state classifier 140 may then output a user status 144 as function of the classification. A "user status 144," as used in this disclosure is a data structure related to the user 120 present confidence. The user status 144 may be represented as a profile containing the plurality of classified user states 136 to the user 120 present confidence relating a plurality of answers received by user 120. As used in this disclosure, a "user state training set" is training data that is used to train user state classifier 140. According to some embodiments, user state 136 training set may include biofeedback signals 132 correlated to answers of known veracity, previous confidence metrics correlated to biofeedback 124, and/or display parameters, for an individual user 120, a cohort of users 120, or a population of users 120. Biofeedback signals 132 correlated to answers of known veracity may include average/standard biological parameters detected when a person answers a question honestly. For example, the measurement of a person's heart rate when they answer honestly their full name. In some embodiments, user state 136 training set may include historic information. "Historic information," as used in this disclosure, is data related to a parameter study. For example, historic information may include studies related to biological responses that occur during polygraph testing. Historic information may include information from eye-related study, speech-related study, circulatory-related study, respiratory-related study, temperature-related study, and the like. User state 136 training set may include any training set and/or training data as described in this disclosure. In some cases, computing device 104 is additionally configured to generate a confidence metric associated with classifying user state 136. As used in this disclosure, a "confidence metric" is a quantified score that is associated with a process, for example a fit or probability of a classification. Confidence metric may be generated and/or output from any machine-learning process as described in this disclosure such as. Confidence metric may be generated using fuzzy sets as described further below.

Still referring to FIG. 1, computing device 104 may be configured to generate classifier 140 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate classifier 140 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, in some cases, apparatus 100 may be configured to communicate feedback characterizing quality of communication with user 120 to one or more users 120. In some cases, feedback characterizing quality of communication with user 120 may be referred to as a communication metric. Feedback characterizing quality of communication with user 120 may include any biofeedback signal 132, user state 136, and/or confidence metric. In some cases, feedback may be provided to a different user 120 than is being presented questions. For example, in an exemplary embodiment where a class of students is receiving questions as part of an educational curriculum, a teacher or professor may have feedback characterizing quality of communication presented to her, for example by way of one or more displays. Feedback can be presented to a user 120 in real-time. Alternatively or additionally, feedback may be presented asynchronously. In some cases, feedback may be used to determine suitability of a subject for a particular task. For instance, in an exemplary embodiment where apparatus 100 is being used with a UAV pilot, feedback may be used to determine if the UAV pilot needs to be replaced. In some cases, apparatus 100 may allow an objective determination (e.g., communication metric) to be made about a subject's ability to remain honest to a task at hand.

Still referring to FIG. 1, in some cases apparatus 100 may be used to store feedbacks characterizing quality of communication. For instance feedbacks may be stored to memory 112. Memory 112 may include any memory 112 component described in this disclosure. Stored feedbacks, in some cases, may be retrieved and analyzed. Analysis may be performed using any method described in this disclosure, including without limitation machine-learning processes. Stored feedbacks may be used to determine trends within the data. In some cases, feedbacks may be aggregated, for example added, multiplied, averaged, or the like. Aggregated feedbacks may include feedbacks from multiple users 120, for instance without limitation multiple users 120 engaged with the same questions. Alternatively or additionally, aggregated feedbacks may include feedbacks from substantially only one user 120, for instance without limitation one user 120 as she engages with a plurality of different questions over time. In some cases, feedbacks characterizing quality of communication of questions may be normalized, for instance by way of statistical methods, such as averaging. In some cases, normalized feedbacks may be used as an objective measure of how a question was received or engaged with by a user 120 or by a plurality of users 120. In some cases, normalized feedbacks may be compared, for example without limitation to determine a quality of a first presentation compared to a second presentation.

With continued reference to FIG. 1, sensor 128 may include at least a speech sensor 128. As used in this disclosure, a "speech sensor 128" is any system or device that is configured or adapted to detect a speech parameter as a function of a speech parameter. In some cases, speech sensor 128 may be configured to detect at least a speech parameter as a function of at least a speech parameter. As used in this disclosure, a "speech parameter" is an element of information associated with speech. An exemplary non-limiting speech parameter is a representation of at least a portion of audible speech, for instance a digital representation of audible speech. In some cases, a speech parameter may be transmitted or represented by a speech signal. A speech signal may include any signal described in this disclosure. As used in this disclosure, a "speech parameter" may include any observable parameter associated with speech, including without limitation audible response and/or acoustic response. Speech response may include pressure changes, for instance audible pressure changes as detectable by a microphone. In some cases, speech parameter may not be directly related to speech, and may include response related to breathing. For example, breathing sounds may be detected by speech sensor 128 and used as speech parameter. In some embodiments, at least a speech sensor 128 may include a bone conductance transducer. In some cases, bone conductance transducer may be configured to detect at least a speech parameter as a function of at least a speech parameter. In some cases, apparatus 100 may utilize communication signals and use them as representation of speech parameters. For instance, in some cases, a person may already be in audible communication with others, through communication microphones. These communication signals may be used by apparatus 100 as speech parameters. In some embodiments at least a sensor 128 may include an electromyography sensor 128.

Figure 2:
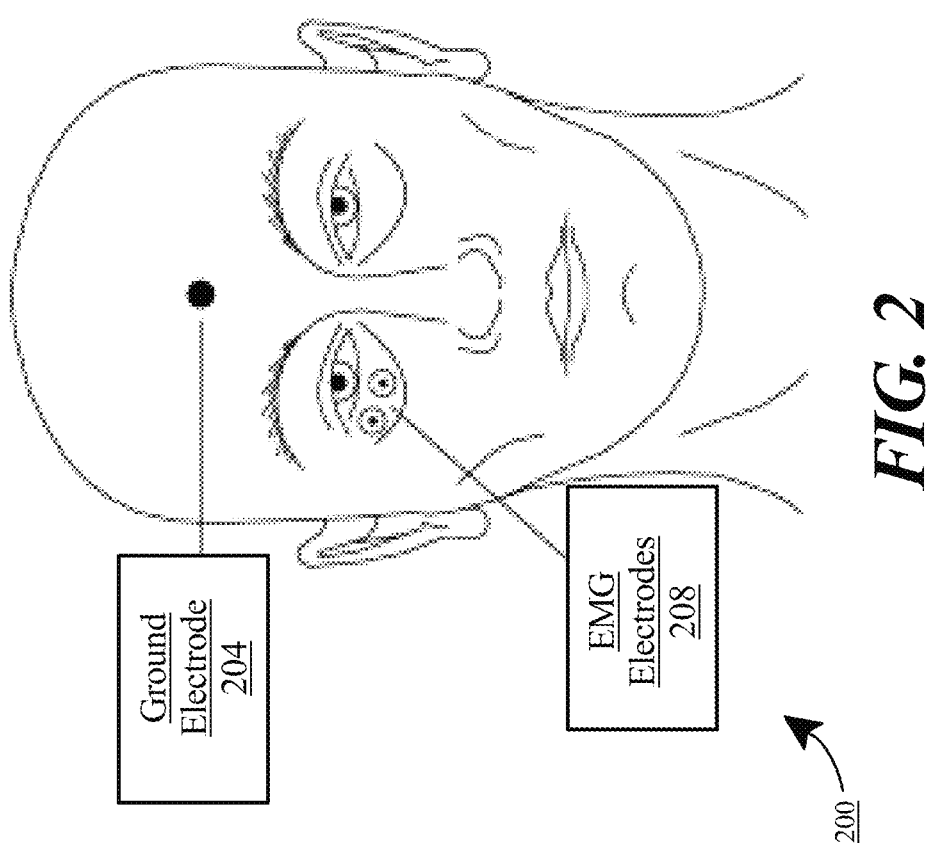
FIG. 2 illustrates exemplary placement of an electromyography sensor.

Referring now to FIG. 2 an exemplary EMG sensor 128 is illustrated. In some cases, electromyography (EMG) may be an electrodiagnostic medicine technique for evaluating and recording electrical activity produced by skeletal muscles. EMG may be performed using an instrument called an electromyograph to produce a record called an electromyogram. An electromyograph may detect electric potential generated by muscle cells, for instance when these cells are electrically or neurologically activated. Resulting electromyographic signals can be analyzed to detect medical abnormalities, activation level, or recruitment order, or to analyze the biomechanics of human or animal movement. In some cases, EMG may also be used as middleware in gesture recognition towards allowing input of physical action to a computing device or as a form of human-computer interaction. In some cases, an EMG sensor 128 may be located about an eye of a user 120 and used to detect eye movements and/or blinks, for instance through detection of electrical activity of extraocular muscles. An EMG sensor 128 may include at least a ground electrode 204 and at least an EMG electrode 208. In some cases, a ground electrode 204 may be placed substantially away from an eye and/or extraocular muscles. In some cases, a ground electrode 204 may be electrically isolated (i.e., floating), thereby allowing detection of muscular electrical activity relative the body rather than relative a ground or other reference. In some cases, EMG signals may be substantially made up of superimposed motor unit action potentials (MUAPs) from several motor units (e.g., muscles). EMG signals can be decomposed into their constituent MUAPs. MUAPs from different motor units tend to have different characteristic shapes, while MUAPs recorded by the same electrode from the same motor unit are typically similar. Notably MUAP size and shape depend on where the electrode is located with respect to muscle fibers and so can appear different if an electrode 204, 208 moves position. EMG decomposition may involve any signal processing methods described in this disclosure, including those below.

With continued reference to FIG. 2, in some case EMG signal rectification may include translation of a raw EMG signal to a signal with a single polarity, for instance positive. In some cases, rectifying an EMG signal may be performed to ensure the EMG signal does not average to zero, as commonly a raw EMG signal may have positive and negative components. According to some embodiments, substantially two types of EMG signal rectification may be used full-wave and half-wave rectification. As used in this disclosure, "full-wave rectification" may add EMG signal below a baseline to the EMG signal above the baseline, thereby resulting in a conditioned EMG signal that is all positive. For example, if baseline of EMG signal is zero, full-wave rectification would be equivalent to taking an absolute value of the EMG signal. According to some embodiments, full-wave rectification may conserve substantially all of EMG signal energy for analysis. As used in this disclosure, "half-wave rectification" discards a portion of EMG signal below baseline. As a result of half-wave rectification, average of EMG signal may no longer be zero; therefore, an EMG signal conditioned by half-wave rectification can be used in further statistical analyses.

Still referring to FIG. 2, in some embodiments, EMG sensor 128 may be used to detect a gaze of user 120 and/or the gaze of the user 120 over time. As used in this disclosure, "gaze" is a direction a user 120 is looking. As used in this disclosure "gaze vector" is a directional vector having a point located at a user's eye (e.g., pupil, retina, or the like) which represents a gaze of the user 120. In some cases, an EMG sensor 128 may be used to detect a gaze of a user 120 over time and this information may be used as input for one or more machine-learning models described herein. For example, in some cases, user's whose gave is infrequently directed at interface 116 may be found to have a relatively lower confidence than those whose gaze is fixed on the interface 116. Alternatively or additionally, in some cases, a user's blink rate as detected by EMG sensor 128 may be used as an input for one or more machine-learning described herein. This is because, it also may be that users 120 who blink more frequently are less honest than those who blink less.

Referring again to FIG. 1, in some embodiments, similar gaze tracking and/or blink tracking functionality may be performed by a user 120 facing camera and machine vision software. An exemplary machine vision camera that may be included as at least a sensor 128 is an OpenMV Cam H7 from OpenMV, LLC of Atlanta, Georgia, U.S.A. OpenMV Cam comprises a small, low power, microcontroller which allows execution of machine vision applications. OpenMV Cam comprises an ARM Cortex M7 processor and a 640× 480 image sensor 128 operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detection motion, for example by way of frame differencing algorithms; marker detection, for example blob detection; object detection, for example face detection; eye tracking; person detection, for example by way of a trained machine learning model; camera motion detection, for example by way of optical flow detection; code (barcode) detection and decoding; image capture; and video recording Still referring to FIG. 1, computing 104 may receive one or more eye parameters in biofeedback 124. In some cases, computing device 104 determine at least an eye pattern as a function of the at least an eye parameter. As used in this disclosure, an "eye pattern" is a representation of an eye-related behavioral parameter. In some cases, an eye pattern may be derived or otherwise determined from an eye parameter. In some cases, eye parameters (e.g., images from optical tracker or electrical signals from electromyography sensor 128) may be used to ascertain eye movements. Eye movements may be divided into fixations and saccades. Fixations may occur when eye gaze pauses in a certain position. Saccades may occur when eye gaze moves to another position. A resulting series of fixations and saccades may be called a scan path. Smooth pursuit describes a scan path of an eye following a moving object. Fixational eye movements include micro saccades: small, involuntary saccades that occur during attempted fixation. Most information from an eye is made available to a viewer during a fixation or smooth pursuit, but not during a saccade. Scan paths may be useful for analyzing cognitive intent, interest, and salience. Other biological factors may affect the scan path as well. In some cases, eye parameter may include blink rate. As used in this disclosure, is any time related variable associated with movement of an eyelid. Exemplary, blink rates include number of blinks over a certain time, average frequency of blinks, amount of time per blink, delay time between stimulation and a blink (e.g., corneal reflex), and the like.

Still referring to FIG. 1, in some embodiments, computing device 104 may determine at least an eye pattern using one or more machine learning processes. For example, in some cases, computing device 104 may receive an eye pattern training data. As used in this disclosure, "eye pattern training data" is a training set that correlates eye parameters to eye patterns. In some cases, eye pattern training data may be compiled from historic information, for instance by a user 120. In some cases, eye pattern training data may be compiled by an unsupervised machine learning process. Eye pattern training data may use eye parameters correlated to eye patterns for one individual user 120, or for a cohort or population of users 120. Historic information may include information from eye-related study. In some cases, historical information may include information captured from use of system 100. Computing device 104 may input eye pattern training data into an eye pattern machine learning algorithm. As used in this disclosure, an "eye pattern machine learning algorithm" is any machine learning algorithm that is configured to train an eye pattern machine learning model using eye pattern training data. Computing device 104 may train an eye pattern machine learning model, as a function of eye pattern machine learning algorithm. As used in this disclosure, "eye pattern machine learning model" is a machine learning model that is configured to take as input at least an eye parameter and output at least a correlated eye pattern. Computing device 104 may determine at least an eye pattern as a function of eye pattern machine learning model and at least an eye parameter.

Still Referring to FIG. 1, computing device 104 may determine at least a speech pattern as a function of the at least a speech parameter from biofeedback 124. As used in this disclosure, a "speech pattern" is a representation of a speech-related behavioral parameter. In some cases, a speech pattern may be derived or otherwise determined from a speech parameter. Exemplary speech patterns include timber, pitch, and cadence of speech. In some cases, speech pattern may be unrelated to content of an actor's speech. Instead, in some cases, speech pattern may be related to changes audible characteristics of actor's speech. In some cases, speech pattern may be derived through analysis of speech parameters, for instance audio analysis described above. Speech pattern may include one or more prosodic variables. As used in this disclosure, "prosodic variables" are variables that relate to spoken syllables or larger speech units. In some cases, speech pattern may include audible variables, for instance pitch, change in pitch, length of units of speech (e.g., syllables), volume, loudness, prominence (i.e., relative volume of a unit speech, timbre, quality of sound, and the like. In some cases, speech pattern may include acoustic terms. Acoustic terms may include without limitation fundamental frequency, duration, intensity, sound pressure, spectral characteristics, and the like. Speech pattern may include speech tempo. As used in this disclosure, "speech tempo" is a measure of a number of speech units within a certain amount of time. Speech tempo may vary within speech of one person, for instance according to context and emotional factors. Speech tempo may have units of syllables per second.

Still referring to FIG. 1, in some embodiments, computing device 104 may be configured to determine a speech pattern by using one or more machine learning processes. For example, in some cases, computing device 104 may receive a speech pattern training data. As used in this disclosure, "speech pattern training data" is a training set that correlates speech parameters to speech patterns. In some cases, speech pattern training data may be compiled from historic information, for instance by a user 120. In some cases, speech pattern training data may be compiled by an unsupervised machine learning process. Speech pattern training data may use speech parameters correlated to speech patterns for one individual user 120, or for a cohort or population of users 120. Historic information may include information from speech-related study. In some cases, historical information may include information captured from use of apparatus 100. Computing device 104 may input speech pattern training data into a speech pattern machine learning algorithm. As used in this disclosure, a "speech pattern machine learning algorithm" is any machine learning algorithm that is configured to train a speech pattern machine learning model using speech pattern training data. Computing device 104 may train a speech pattern machine learning model, as a function of speech pattern machine learning algorithm. As used in this disclosure, "speech pattern machine learning model" is a machine learning model that is configured to take as input at least a speech parameter and output at least a correlated speech pattern. Computing device 104 may determine at least a speech pattern as a function of speech pattern machine learning model and at least a speech parameter. Computing device 104 may determine an eye pattern and speech using one or more machine learning processes as described in in U.S. Nonprovisional patent application. Ser. No. 17/731,4935, entitled "SYSTEMS AND METHODS FOR DETERMINING ACTOR STATUS ACCORDING TO BEHAVIORAL PHENOMENA," the entirety of which is incorporated herein by reference.

Still referring to FIG. 1, in some embodiments, a user's position, habiliment, and/or posture may be detected by at least a sensor 128. For example, in some cases, a machine vision camera, like that described above may be employed to perform the detection. Alternatively or additionally, in some cases, range-imaging or 3D camera may be used for this purpose. An exemplary range-imaging camera that may be included as an at least a sensor is Intel® RealSense™ D430 Module, from Intel® of Mountainview, California, U.S.A. D430 Module comprises active infrared (IR) illumination and a stereoscopic camera, having global shutters and frame rate of up to 90 fps. D430 Module provide a field of view (FOV) of 85.2° (horizontal) by 58° (vertical) and an image resolution of 0×720. Range-sensing camera may be operated independently by dedicated hardware, or, in some cases, range-sensing camera may be operated by a computing device. In some cases, range-sensing camera may include software and firmware resources (for execution on hardware, such as without limitation dedicated hardware or a computing device). D430 Module may be operating using software resources including Intel® RealSense™ SDK 2.0, which include opensource cross platform libraries With continued reference to FIG. 1, sensor 128 may include a cutaneous sensor 128. As used in this disclosure, a "cutaneous sensor" is a device that is configured to detect a cutaneous parameter as a function of a cutaneous parameter. Cutaneous sensor 128 may be configured to detect at least a cutaneous parameter as a function of a cutaneous parameter. As used in this disclosure, a "cutaneous parameter" is a representation of a cutaneous parameter. Exemplary cutaneous parameters include, without limitation, measures skin temperature, galvanic skin response, and the like. As used in this disclosure, a "cutaneous parameter" is an occurrence that relates to, or is in anyway associated with, skin. Exemplary cutaneous parameter includes, without limitation, skin temperature, electrical conductivity of skin, skin moisture, galvanic skin response and the like.

Still referring to FIG. 1, in some embodiments of apparatus 100, cutaneous sensor 128 may include a skin temperature sensor 128. As used in this disclosure, a "skin temperature sensor" is a device that is configured to detect a skin temperature parameter is a function of a skin temperature. Skin temperature sensor 128 may be configured to detect at least a skin temperature parameter as a function of at least a skin temperature. As used in this disclosure, a "skin temperature parameter" is a representation of a skin temperature. As used in this disclosure, "skin temperature" is a thermal characteristic of skin. In some cases, variability in skin temperature may indicate changes in cardiac output. For instance, increased skin temperature may result for increased blood flow which may indicate increased heart rate and user 120 stress. In some cases, apparatus 100 may additionally include at least an environmental temperature sensor 128. As used in this disclosure, an "environmental temperature sensor 128" is a device that is configured to detect an environmental temperature parameter as a function of an environmental temperature. Environmental temperature sensor 128 may be configured to detect an environmental temperature parameter as a function of an environmental temperature. As used in this disclosure, an "environmental temperature parameter" is a representation of an environmental temperature. As used in this disclosure, an "environmental temperature" is a thermal characteristic of an environment. In some cases, at least a cutaneous parameter is a function of at least a skin temperature parameter and at least an environmental temperature parameter. For example without limitation, in some cases, skin temperature parameter may be determined with reference to an environmental temperature parameter. For instance, skin temperature of a skin may be determined relative an ambient air temperature measured proximal the skin.

Still referring to FIG. 1, in an embodiment, sensor 128 may contact a locus on the exterior body surface where substantially no muscle is located between the exterior body surface and an underlying bone structure, meaning muscle is not located between the exterior body surface and an underlying bone structure and/or any muscle tissue located there is unnoticeable to a user 120 as a muscle and/or incapable of appreciably flexing or changing its width in response to neural signals; such a locus may include, as a non-limiting example, locations on the upper cranium, forehead, nose, behind the ear, at the end of an elbow, on a kneecap, at the coccyx, or the like. Location at a locus where muscle is not located between exterior body surface and underlying bone structure may decrease reading interference and/or inaccuracies created by movement and flexing of muscular tissue. Sensor 128 may contact a locus having little or no hair on top of skin. Sensor 128 may contact a locus near to a blood vessel, such as a locus where a large artery such as the carotid artery or a branch thereof, or a large vein such as the jugular vein, runs near to skin or bone at the location; in an embodiment, such a position may permit at least a sensor 128 to detect circulatory parameters as described further below.

Still referring to FIG. 1, at least a sensor 128 may include an optical sensor 128, which detects light emitted, reflected, or passing through human tissue. Optical sensor 128 may include a near-infrared spectroscopy sensor 128 (NIRS). A NIRS, as used herein, is a sensor 128 that detects signals in the near-infrared electromagnetic spectrum region, having wavelengths between 780 nanometers and 2,500 nanometers.

Figure 3:
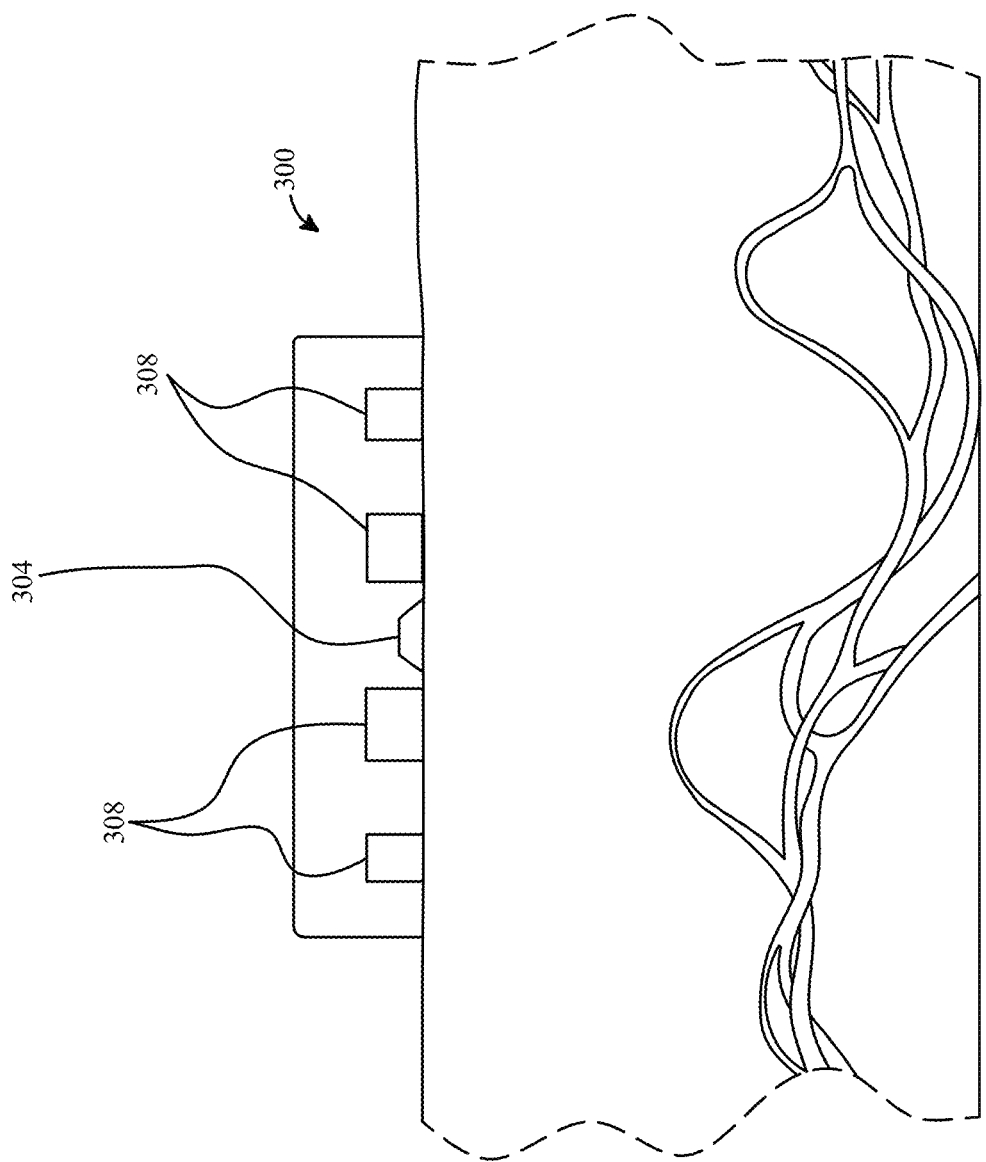
FIG. 3 is a schematic illustration of an exemplary embodiment of a near-infrared spectroscopy sensor.

Referring now to FIG. 3, FIG. 3 illustrates an exemplary embodiment of a NIRS 300 against an exterior body surface, which may include skin. NIRS 300 may include a light source 304, which may include one or more light-emitting diodes (LEDs) or similar element. Light source 304 may, as a non-limiting example, convert electric energy into near-infrared electromagnetic signals. Light source 304 may include one or more lasers. NIRS 300 may include one or more detectors 308 configured to detect light in the near-infrared spectrum. Although the wavelengths described herein are infrared and near-infrared, light source 304 may alternatively or additionally emit light in one or more other wavelengths, including without limitation blue, green, ultra-violet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation $CO_2$ saturation levels, state of hemoglobin as opposed to blood oxygen saturation generally. One or more detectors 308 may include, without limitation, charge-coupled devices (CCDs) biased for photon detection, indium gallium arsenide (InGaAs) photodetectors, lead sulfide (PbS) photodetectors, or the like. NIRS 300 may further include one or more intermediary optical elements (not shown), which may include dispersive elements such as prisms or diffraction gratings, or the like. In an embodiment, NIRS 300 may be used to detect one or more circulatory parameters. A "circulatory parameter," also referred to as a blood parameter, as used in this disclosure, is a parameter describing the state of blood vessels. For example, arteries, veins, or capillaries, any datum describing the rate, volume, pressure, pulse rate, or other state of flow of blood or other fluid through such blood vessels, chemical state of such blood or other fluid, or any other parameter relative to health or current physiological state of user 120 as it pertains to the cardiovascular system. As a non-limiting example, at least a circulatory parameter may include a blood oxygenation level of user's blood. At least a circulatory parameter may include a pulse rate a "pulse rate," as sued in this disclosure, is the rate at which a person's heart beats. At least a circulatory parameter may include a blood pressure level. A "blood pressure level," as used in this disclosure, is the measurement of the force of circulating blood on the walls of the arteries. At least a circulatory parameter may include heart rate variability and rhythm. "Heart rate variability," as used in this disclosure, is a measure of the variation in time between each heartbeat. "Heart rate rhythm," as used in this disclosure, is the time pattern in which a heart beats. At least a circulatory parameter may include a plethysmograph describing user 120 blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse oxygen level (for instance by detecting plethysmograph amplitude), pulse rate (for instance by detecting plethysmograph frequency), heart rate variability and rhythm (for instance by tracking pulse rate and other factors over time), and blood pressure, among other things. At least a sensor 128 may include at least two sensor 128s mounted on opposite sides of user's cranium. Further disclosure related to NIRS sensor 128 may be found in U.S. patent application Ser. No. 16/859,483, entitled "SYSTEMS AND METHODS FOR MEASURING PHYSIOLOGICAL PARAMETERS," the entirety of which is incorporated herein by reference.

Figure 4:
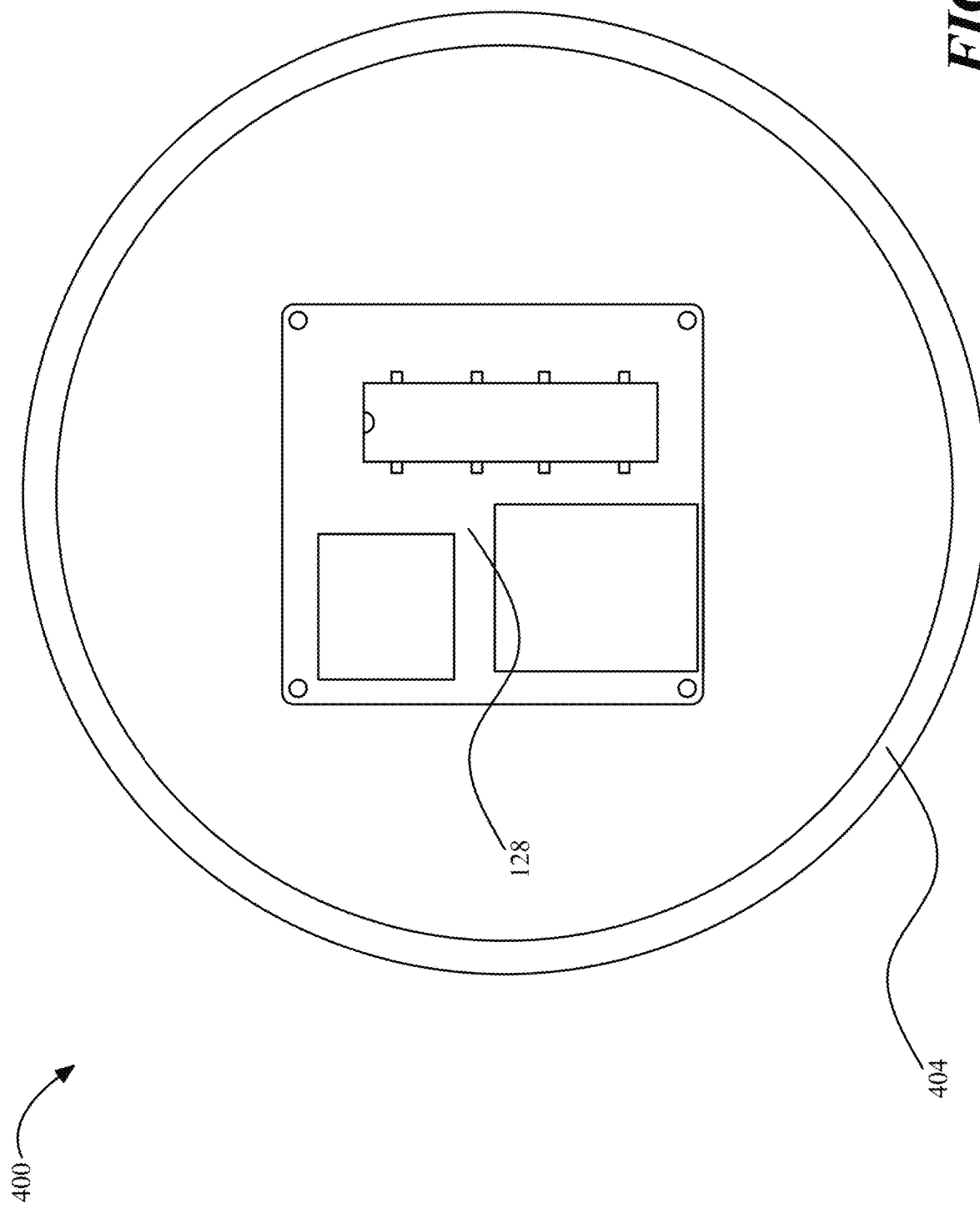
FIG. 4 is a schematic diagram illustrating an exemplary embodiment of a combined exhaled air and environmental gas sensor apparatus.

Referring now to FIG. 4, combined exhaled air and environmental gas sensor apparatus 400 for mobile respiratory equipment is illustrated. Apparatus 400 includes a housing 404, within which one or more electronic components are positioned. One or more electric components include a sensor 128. Sensor 128 may include an exhaled air and environmental gas sensor. Housing 404 may be constructed of any suitable material or combination of materials, including without limitation metal, metal such as aluminum, titanium, steel, or the like, plant materials including bamboo and/or wood, polymer materials such as polycarbonate, polymethyl methacrylate, acrylonitrile butadiene styrene (ABS), or the like, synthetic fibers such as carbon fiber, silicon carbide fiber, metallic fiber, or the like, composite materials such as fiberglass, laminated fiberglass, plywood, or the like, or any combination of the above. Housing 404 may be manufactured in any suitable process including molding such as injection molding, additive manufacturing such as "three-dimensional printing" and/or stereolithography, subtractive processes such as machining, and/or any other process or combination of processes. Housing 404 may include a sensor-bearing surface on or to which one or more electrical components including sensor 128 may be attached. A sensor-bearing surface may be positioned opposite a port aperture as described in further detail below.

Figure 5B:
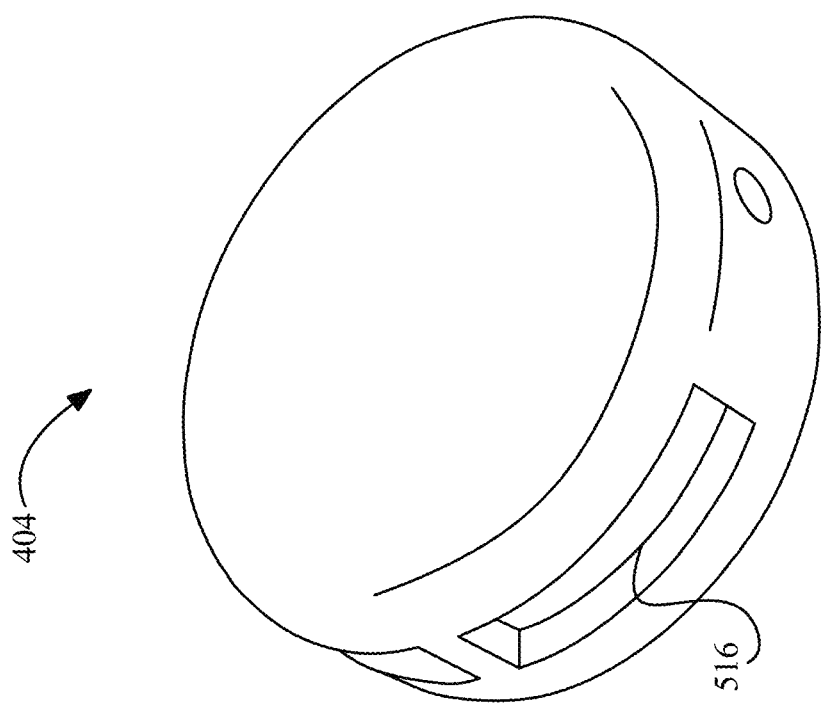
FIG. 5B is a schematic diagram illustrating an exemplary embodiment of a housing.
Figure 5A:
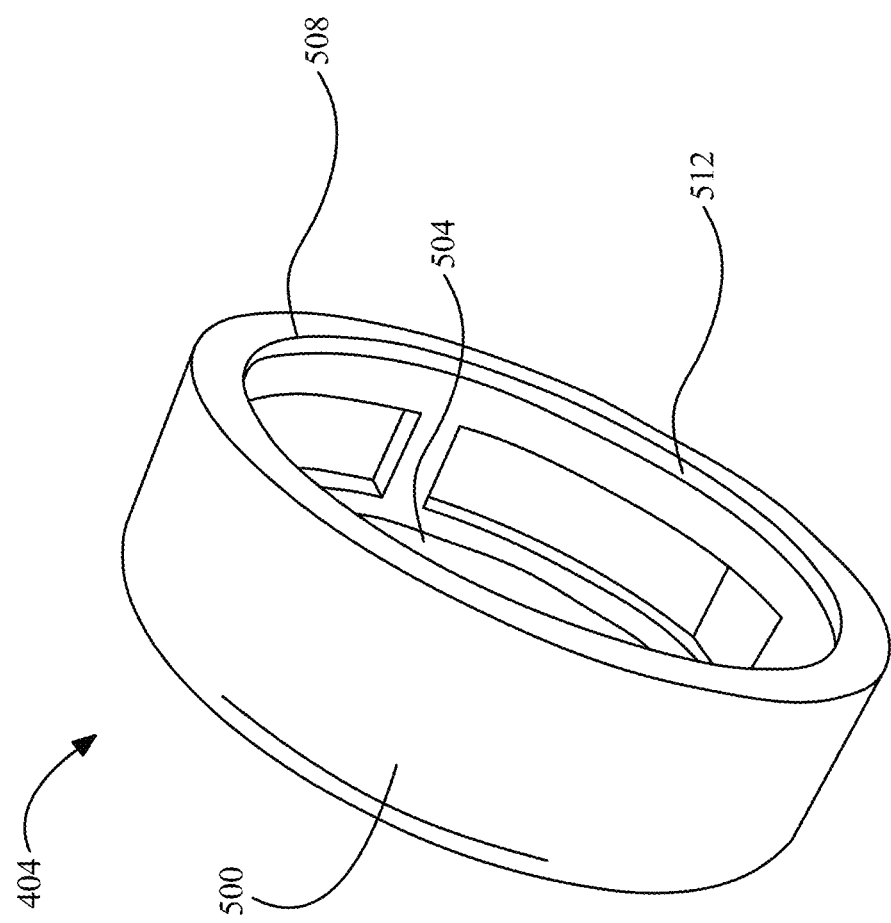
FIG. 5A is a schematic diagram illustrating an exemplary embodiment of a housing.

Referring now to FIG. 5A, a perspective view of an exemplary embodiment of a housing 404 is illustrated. Housing 404 may include an exterior surface 500, an interior surface 504, an interior space surrounded by interior surface 504, and one or more apertures. Housing 404 may have any suitable shape, including a shape of a cap to be placed over a respiratory exhaust port as described in further detail below. Housing 404 may be substantially cylindrical and may have one or more rounded edges. Housing 404 includes a port aperture 508. Port aperture 508 is an aperture that receives exhaled breath from a respiratory exhaust port as described in further detail below, admitting the exhaled breath into interior space of housing 404. Housing 404 further includes a connector 512, which may be located at port aperture 508. A "connector," as used in this disclosure, is a structural feature and/or component that affixes one aperture, opening, port, or the like to another in a way that permits flow of fluids such as liquid and/or gases to flow from one aperture, opening, port, or the like to another. Connector 512 is configured to attach port aperture 508 to exhaust port. Connector 512 may include, without limitation, a rim that fits and/or snaps over a feature of exhaust port to affix port aperture 508 thereto; connector 512 may alternatively or additionally include fastener, such as a bold or screw that inserts through a hole in housing 404 and screws into a reciprocally threaded hole in exhaust port. Connector 512 may include threading around port aperture 508 that engages reciprocal threading at exhaust port. Connector 512 may include and/or be combined with adhesives, sealants, or the like. Connector 512 may permit repeated detachment and reattachment or may affect a permanent connection between port aperture 508 and exhaust port. Persons skilled in the art, upon reviewing the entirety of this disclosure, will be aware of various alternative or additional structures and/or components that may be used for connector 512. Port aperture 508 may be located opposite a sensor-bearing surface; for instance, the sensor-bearing surface may be located on interior surface 504 at a distal end of housing 404, while port aperture 508 may be located at a proximal end of housing 404.

Referring now to FIG. 5B, housing 404 includes at least an ambient aperture 516 connecting to an exterior environment. An "exterior environment," as used in this disclosure, means air that is exterior to an element of mobile respiratory equipment as described below; for instance, where mobile respiratory equipment is a respirator mask, exterior environment may include air outside of the mask and around a person wearing the mask, as opposed to air or gas between the mask and mouth or nose of the person. At least an ambient aperture 516 includes an opening connecting interior space to exterior environment. At least an ambient aperture 516 may permit air to travel freely between interior space and exterior environment.

Figure 6:
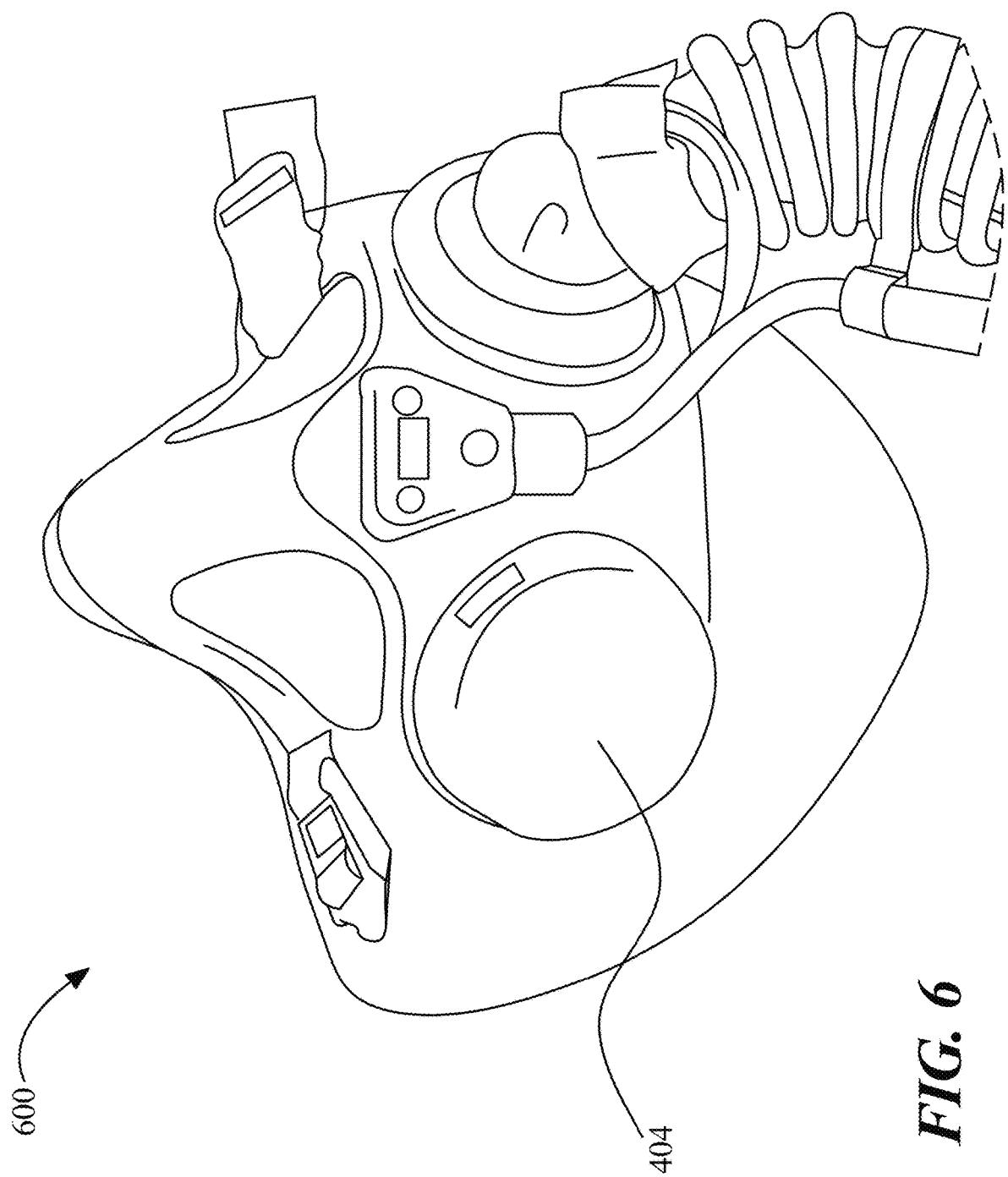
FIG. 6 is a schematic diagram illustrating an exemplary embodiment of a combined exhaled air and environmental gas sensor apparatus.

In an embodiment, and referring now to FIG. 6, housing 404 may be attached to an exhaust port of a mobile respiratory device 600. A "mobile respiratory device," as used herein, is a device worn on or about a face of a person, which aids in respiration, for instance when the person is in an environment where oxygen may be scarce or where other gases or particular matter such as carbon dioxide, carbon dioxide, toxic gases, droplets or fumes, or other elements that may interfere with respiration, and/or gases having ambient temperatures capable of harming a person when inhaled. Such an environment may include, without limitation, a cockpit of an aircraft such as a military aircraft, an artificially or naturally formed tunnel with an atmosphere that makes breathing difficult, such as an anoxic atmosphere, an atmosphere containing poisonous or otherwise problematic gases such as sulfur dioxide, carbon dioxide, carbon monoxide, or the like, a location at a high altitude such as a mountaintop, a location of a chemical spill and/or the like.

Still referring to FIG. 6, mobile respiratory device 600 may include, without limitation, a gas mask such as a cannister mask, a self-contained breathing apparatuses (SCBA) such as those used by firefighters, self-contained underwater breathing apparatuses (SCUBA), supplied-air respirators (SAR), particulate respirators, chemical cartridge respirators, powered air-purifying respirators (PAPRs), respirators included as part of a protective suit, airline respirators, N-95 or other NIOSH approved respirators, and/or other devices worn on and/or over and at least partially occluding the face to aid in respiration.

With continued reference to FIG. 6, an "exhaust port," as used in this disclosure, is an outlet that permits air exhaled by a user 120 to escape from a mobile respiratory device 600. Exhaust port may include a valve such as a check-valve or other one-way valve to prevent air from entering a mobile respiratory device 600 from environment. Exhaust port may include, for instance, an exhale valve of a respirator mask or other such design. Exhaust port may also be an inlet port; for instance, air may be filtered while breathing in through the port and then exhaled, with or without filtering, via a valve at the same port. In operation, housing 404 with port aperture 508 and ambient aperture 516 may form a plenum in which exhaled and ambient air may flow freely by sensor 128, permitting sensation of both breath composition and environmental air composition. Further disclosure related to combined exhaled gas and environmental gas sensor 128 may be found in U.S. patent application Ser. No. 16/933,680, entitled "COMBINED EXHALED AIR AND ENVIRONMENTAL GAS SENSOR APPARATUS," the entirety of which is incorporated herein by reference. In some embodiments, at least a sensor 128 may include an inspirate sensor 128.

Figure 7:
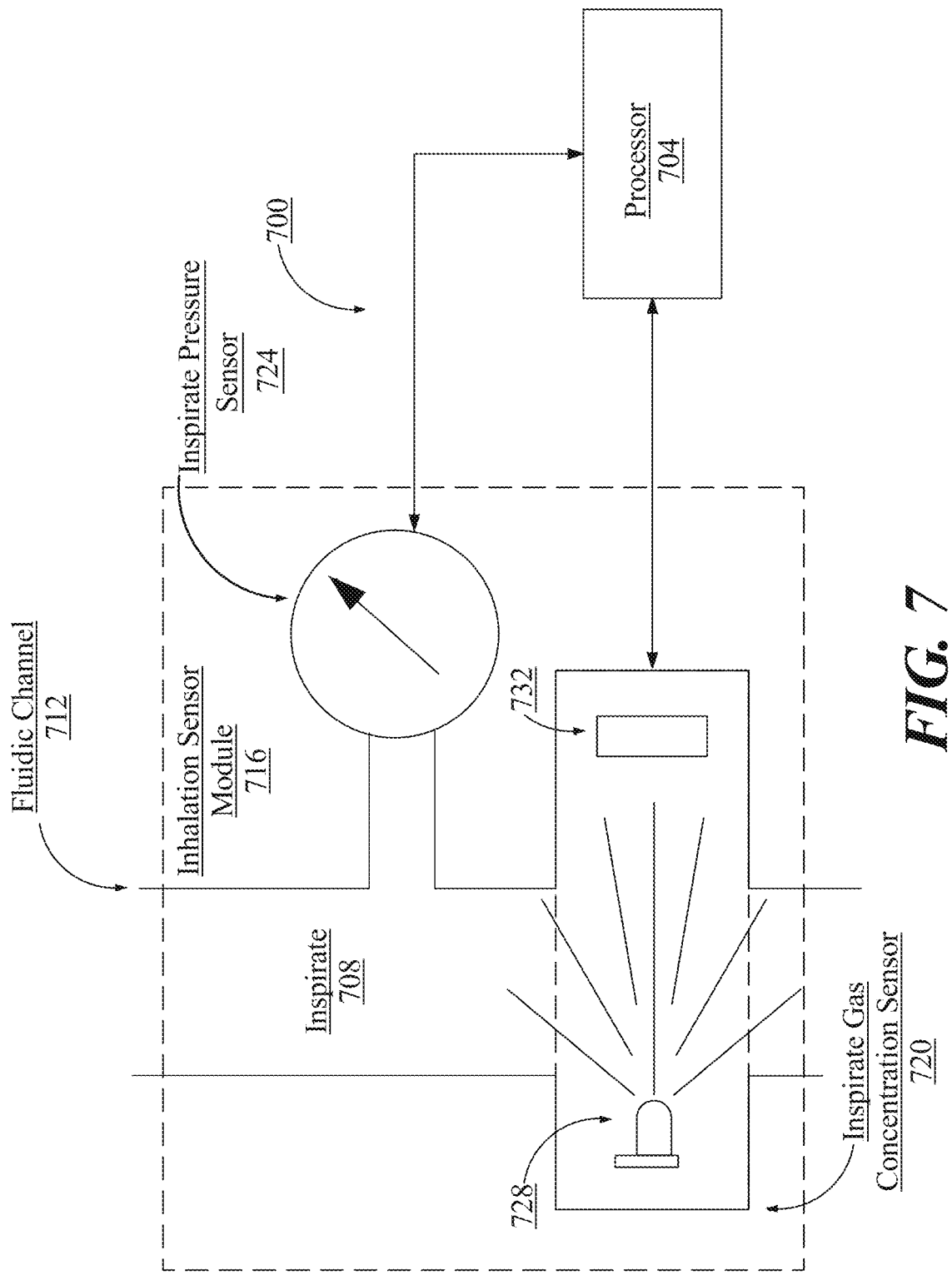
FIG. 7 is a block diagram illustrating an exemplary inhalation sensor module.

Referring now to FIG. 7, an exemplary inspirate sensor 700 is illustrated. Sensor 128 may include inspiration sensor 700. In some embodiments, inspirate sensor 700 may include a processor 704 for making determinations as a function of sensed parameters associated with at least an inspirate 708. in communication with an exemplary inhalation sensor module 708. In some cases, at least a portion of an at least an inspirate 708 is contained within a fluidic channel 712. An exemplary inhalation sensor module 716 is shown in fluid communication with fluidic channel 712. In some cases, inhalation sensor module may include at least a gas concentration sensor 720. In some cases, inhalation sensor module 716 may include at least an inspirate pressure sensor 724. Inspirate gas concentration sensor 720 may include any gas concentration sensor, for instance those described in this application. In some cases, inspirate gas concentration sensor 720 may include an optical gas concentration sensor. Non-limiting optical gas concentration sensors include infrared transmission and/or absorbance spectroscopy type sensors and fluorescence excitation type sensors. Commonly, an optical gas concentration sensor may include a radiation source 728 and a radiation detector 732. In some versions, radiation source 728 may include a light source 728 that may generate a light and illuminate at least a portion of at least an inspirate 708. Radiation source 728 may generate any of a non-limiting list of lights, including coherent light, non-coherent light, narrowband light, broadband light, pulsed light, continuous wave light, pseudo continuous wave light, ultraviolet light, visible light, and infrared light. In some cases, radiation source 728 may include an electromagnetic radiation source that may generate an electromagnetic radiation and irradiate at least a portion of at least an inspirate 708. Radiation source 728 may generate any of a non-limiting list of radiations including radio waves, microwaves, infrared radiation, optical radiation, ultraviolet radiation, X-rays, gamma-rays, and light. Non-limiting examples of radiation sources 728 include lasers, light emitting diodes (LEDs), light emitting capacitors (LECs), flash lamps, antennas, and the like. In some cases, radiation detector 732 may be configured to detect light and/or radiation that has interacted directly or indirectly with at least a portion of at least an inspirate 708. Non-limiting examples of radiation detectors 732 include photodiodes, photodetectors, thermopiles, pyrolytic detectors, antennas, and the like. In some cases, a radiation amount detected by radiation detector 732 may be indicative of a concentration of a particular gas in at least a portion of at least an inspirate 708. For example, in some exemplary embodiments, radiation source 728 may include an infrared light source operating at a wavelength about 4.6 μm and radiation detector may include a photodiode sensitive over a range encompassing 4.6 μm. An exemplary infrared light source may include an LED comprising InAsSb/InAsSbP heterostructures, for example LED46 from Independent Business Scientific Group (IBSG) of Saint Petersburg, Russia. An exemplary infrared detector may include a mercury cadmium telluride photodiode, for example UM-I-6 HgCdTe from Boston Electronics of Brookline, Massachusetts. In some cases, an amount of radiation at least a specific wavelength absorbed, scatter, attenuated, and/or transmitted may be indicative of a gas concentration.

With continued reference to FIG. 7, in some cases, inspirate concentration sensor 720 may include an infrared point sensor. An infrared (IR) point sensor may use radiation passing through a known volume of gas, for example at least an inspirate 708. In some cases, detector 732 may be configured to detect radiation after passing through gas at a specific spectrum. As energy from infrared may be absorbed at certain wavelengths, depending on properties of at least an inspirate 720. For example, carbon monoxide absorbs wavelengths of about 4.2-4.5 µm. In some cases, detected radiation within a wavelength range (e.g., absorption range) may be compared to a wavelength outside of the wavelength range. A difference in detected radiation between these two wavelength ranges may be found to be proportional to a concentration of gas present. In some embodiments, an infrared image sensors may be used for active and/or passive imaging. For active sensing, radiation source 728 may include a coherent light source (e.g., laser) which may be scanned across a field of view of a scene and radiation detector 732 may be configured to detect backscattered light at an absorption wavelength of a specific target gas. In some cases, radiation detector 732 may include an image sensor, for example a two-dimensional array of radiation sensitive devices, for example arranged as pixels. Passive IR imaging sensors may measure spectral changes at each pixel in an image and look for specific spectral signatures that indicate presence and/or concentration of target gases.

With continued reference to FIG. 7, in some cases, inspirate gas concentration sensor 720 may include an oxygen sensor. An exemplary oxygen sensor may include an electro-galvanic sensor. For example, an electro-galvanic oxygen sensor may be used to measure a concentration of oxygen within at least an inspirate 708. In some cases, an electro-galvanic oxygen sensor may include a lead/oxygen galvanic cell, within which oxygen molecules are dissociated and reduced to hydroxyl ions at a cathode. Hydroxyl ions may diffuse through an electrolyte and oxidize a lead anode. A current proportional to a rate of oxygen consumption may be generated when cathode and anode are electrically connected through a resistor. Current may be sensed by known current sensing methods, for example without limitation those described in this disclosure, to produce an electrical signal proportional to a concentration of oxygen, for example oxygen within at least an inspirate. Another exemplary oxygen sensor may include a lambda sensor, for example a zirconia sensor, a wideband zirconia sensor, and/or a titania sensor. A lambda sensor may be configured to sense a quantity of oxygen in a gas (e.g., at least an inspirate 708) relative another gas, for example air within an environment (e.g., cabin air) and transmit an analog voltage correlated to the sensed relative quantity of oxygen. Analog voltage transmitted by a lambda sensor may be processed by any data or signal processing methods discussed herein, for example through amplification and/or analog-to-digital conversion.

In another exemplary embodiment, inspirate concentration sensor 720 may include an optical sensor configured to sense oxygen concentration. In some cases, a chemical film is configured to be in contact with a gas (e.g., at least an inspirate 708). Chemical film may have fluorescence properties which are dependent upon presence and/or concentration of oxygen. Radiation detector 732 may be positioned and configured, such that it is in sensed communication with chemical film. Radiation source 728 may irradiate and/or illuminate chemical film with radiation and/or light having properties (e.g., wavelength, energy, pulse duration, and the like) consistent with exciting fluorescence within the chemical film. In some cases, fluorescence may be at a maximum when there is no oxygen present. For example, oxygen molecules may collide with chemical film and quench photoluminescence resulting from fluorescent excitation. A number of $O_2$ molecules colliding with chemical film may be correlated with a concentration of oxygen within a gas (e.g., inspirate 708). Fluorescence properties as sensed by optical detector 732 may therefore be related to oxygen concentration. Fluorescence properties may include emission duration, fluorescence energy, and the like. In some cases, detected optical signal (fluorescence) to oxygen concentration may not be linear. For instance, an optical oxygen sensor may be most sensitive at low oxygen concentration; that is, sensitivity decreases as oxygen concentration increases, following a known Stern-Volmer relationship. In some cases, an optical oxygen sensor is advantageous as substantially no oxygen may be consumed, during sensing. In some cases, planar optical oxygen sensors (i.e., optodes) may be used to detect a spatial distribution of oxygen concentrations over an area, for example as a two-dimensional image. Based on the same principle, radiation detector 732 may include a digital camera that may be used to capture fluorescence intensities over a specific area.

With continued reference to FIG. 7, inhalation sensor module 716 may include at least an inspirate pressure sensor 724, which is fluidic communication with at least an inspirate 708, for example by way of at least a fluidic channel 712. In some cases, at least an inspirate pressure sensor 716 may be configured to sense and transmit at least an inspirate pressure parameter as a function of a pressure of at least an inspirate 708. In some cases, inhalation pressure sensor 724 may include any type of pressure sensor described in this disclosure. Inhalation pressure sensor 724 may be a force collector type pressure sensor. Alternatively, in some case, inhalation pressure sensor 724 may be a pressure sensor type that does not use force collection. Further disclosure related to the inhalation sensor may be found in U.S. patent application Ser. No. 17/333,169, entitled "SYSTEMS AND METHODS FOR INSPIRATE SENSING TO DETERMINE A PROBABILITY OF AN EMERGENT PHYSIOLOGICAL STATE," the entirety of which is incorporated herein by reference.

Figure 8:
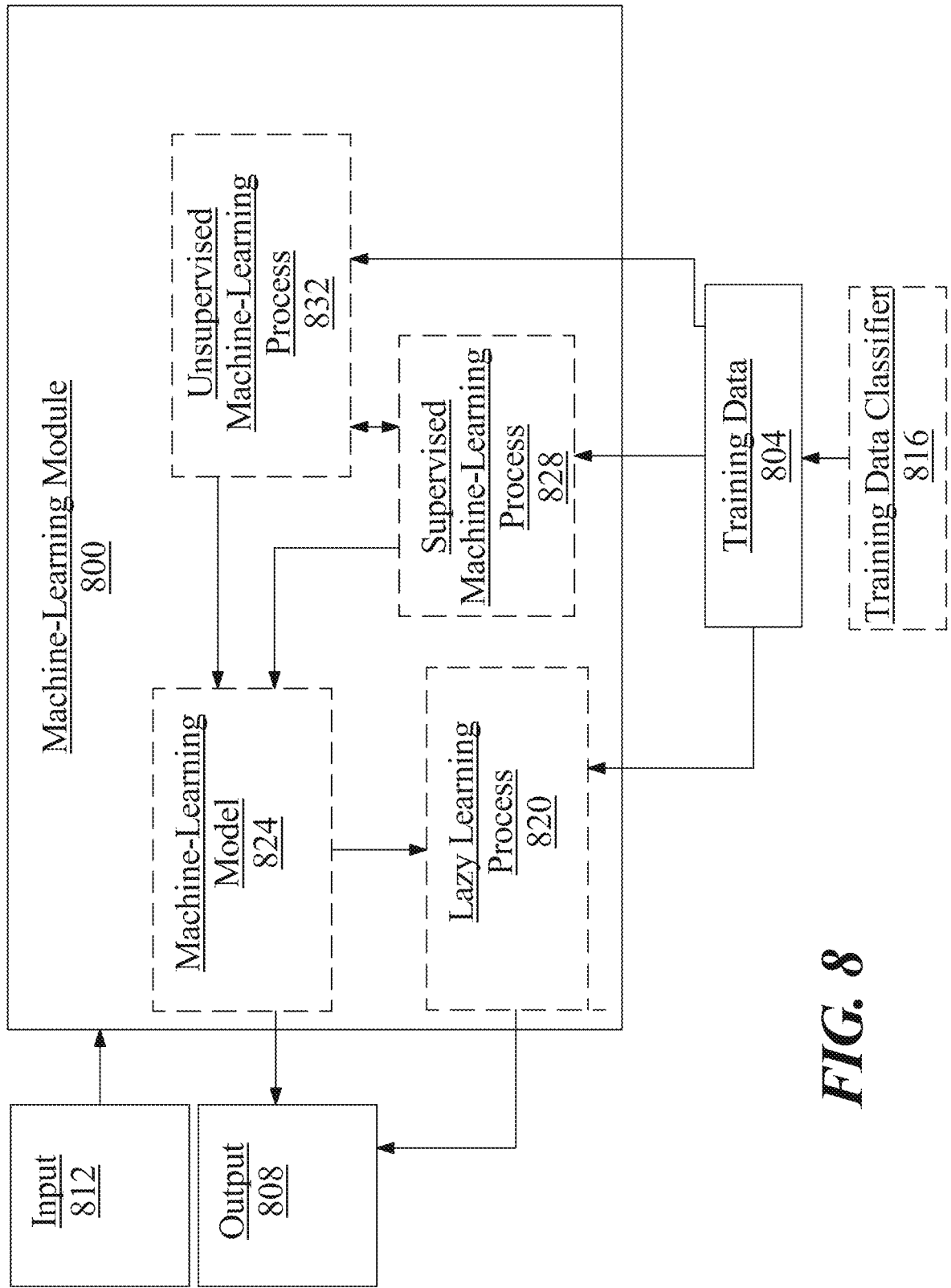
FIG. 8 is a block diagram of an exemplary machine-learning process.

Referring now to FIG. 8, an exemplary embodiment of a machine-learning module 800 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 804 to generate an algorithm that will be performed by a computing device/module to produce outputs 808 given data provided as inputs 812; this is in contrast to a non-machine learning software program where the commands to be executed are determined in advance by a user 120 and written in a programming language.

Still referring to FIG. 8, "training data," as used herein, is data containing correlations that a machine-learning process may use to model relationships between two or more categories of data elements. For instance, and without limitation, training data 804 may include a plurality of data entries, each entry representing a set of data elements that were recorded, received, and/or generated together; data elements may be correlated by shared existence in a given data entry, by proximity in a given data entry, or the like. Multiple data entries in training data 804 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 804 according to various correlations; correlations may indicate causative and/or predictive links between categories of data elements, which may be modeled as relationships such as mathematical relationships by machine-learning processes as described in further detail below. Training data 804 may be formatted and/or organized by categories of data elements, for instance by associating data elements with one or more descriptors corresponding to categories of data elements. As a non-limiting example, training data 804 may include data entered in standardized forms by persons or processes, such that entry of a given data element in a given field in a form may be mapped to one or more descriptors of categories. Elements in training data 804 may be linked to descriptors of categories by tags, tokens, or other data elements; for instance, and without limitation, training data 804 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 8, training data 804 may include one or more elements that are not categorized; that is, training data 804 may not be formatted or contain descriptors for some elements of data. Machine-learning algorithms and/or other processes may sort training data 804 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 804 to be made applicable for two or more distinct machine-learning algorithms as described in further detail below. Training data 804 used by machine-learning module 800 may correlate any input data as described in this disclosure to any output data as described in this disclosure. As a non-limiting illustrative example biofeedback signals 132 may be categorized according to user 120 and/or user 120 cohort. In some cases, a machine-learning model may need to be trained using training substantially from only one user 120. Alternatively or additionally, in some cases, training data may include biofeedback signals 132 from a population of users 120.

Further referring to FIG. 8, training data may be filtered, sorted, and/or selected using one or more supervised and/or unsupervised machine-learning processes and/or models as described in further detail below; such models may include without limitation a training data classifier 816. Training data classifier 816 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 800 may generate a classifier using a classification algorithm, defined as a process whereby a computing device and/or any module and/or component operating thereon derives a classifier from training data 804. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 8, machine-learning module 800 may be configured to perform a lazy-learning process 820 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 804. Heuristic may include selecting some number of highest-ranking associations and/or training data 804 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 8, machine-learning processes as described in this disclosure may be used to generate machine-learning models 824. A "machine-learning model," as used in this disclosure, is a mathematical and/or algorithmic representation of a relationship between inputs and outputs, as generated using any machine-learning process including without limitation any process as described above and stored in memory 112; an input is submitted to a machine-learning model 824 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 824 may be generated by creating an artificial neural network, such as a convolutional neural network comprising an input layer of nodes, one or more intermediate layers, and an output layer of nodes. Connections between nodes may be created via the process of "training" the network, in which elements from a training data 804 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 8, machine-learning algorithms may include at least a supervised machine-learning process 828. At least a supervised machine-learning process 828, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 804. Persons skilled in the art, upon reviewing the entirety of this disclosure, will be aware of various possible variations of at least a supervised machine-learning process 828 that may be used to determine relation between inputs and outputs. Supervised machine-learning processes may include classification algorithms as defined above.

Further referring to FIG. 8, machine learning processes may include at least an unsupervised machine-learning processes 832. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 8, machine-learning module 800 may be designed and configured to create a machine-learning model 824 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include the least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 8, machine-learning algorithms may include, without limitation, linear discriminant analysis. Machine-learning algorithms may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 9:
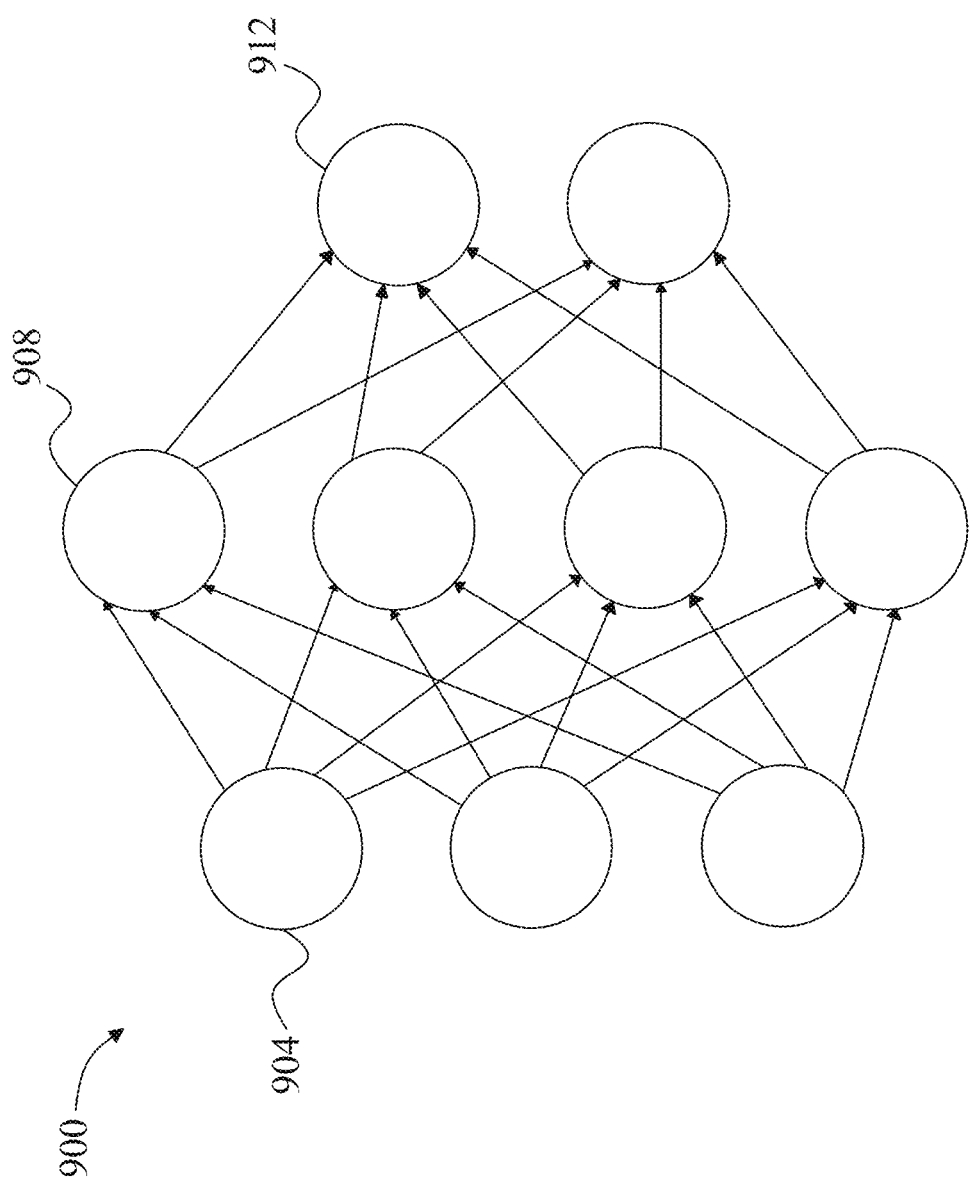
FIG. 9 is a schematic diagram of an exemplary embodiment of a neural network.

Referring now to FIG. 9 an exemplary embodiment of neural network 900 is illustrated. Neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 904, one or more intermediate layers 908, and an output layer of nodes 912. Connections between nodes may be created via the process of "training" the network, in which elements from a training dataset are applied to input nodes 904, a suitable training algorithm (such as Levenberg-Marquardt, conjugate gradient, simulated annealing, or other algorithms) is then used to adjust the connections and weights between nodes in adjacent layers 908 of the neural network to produce the desired values at output nodes 912. This process is sometimes referred to as deep learning.

Figure 10:
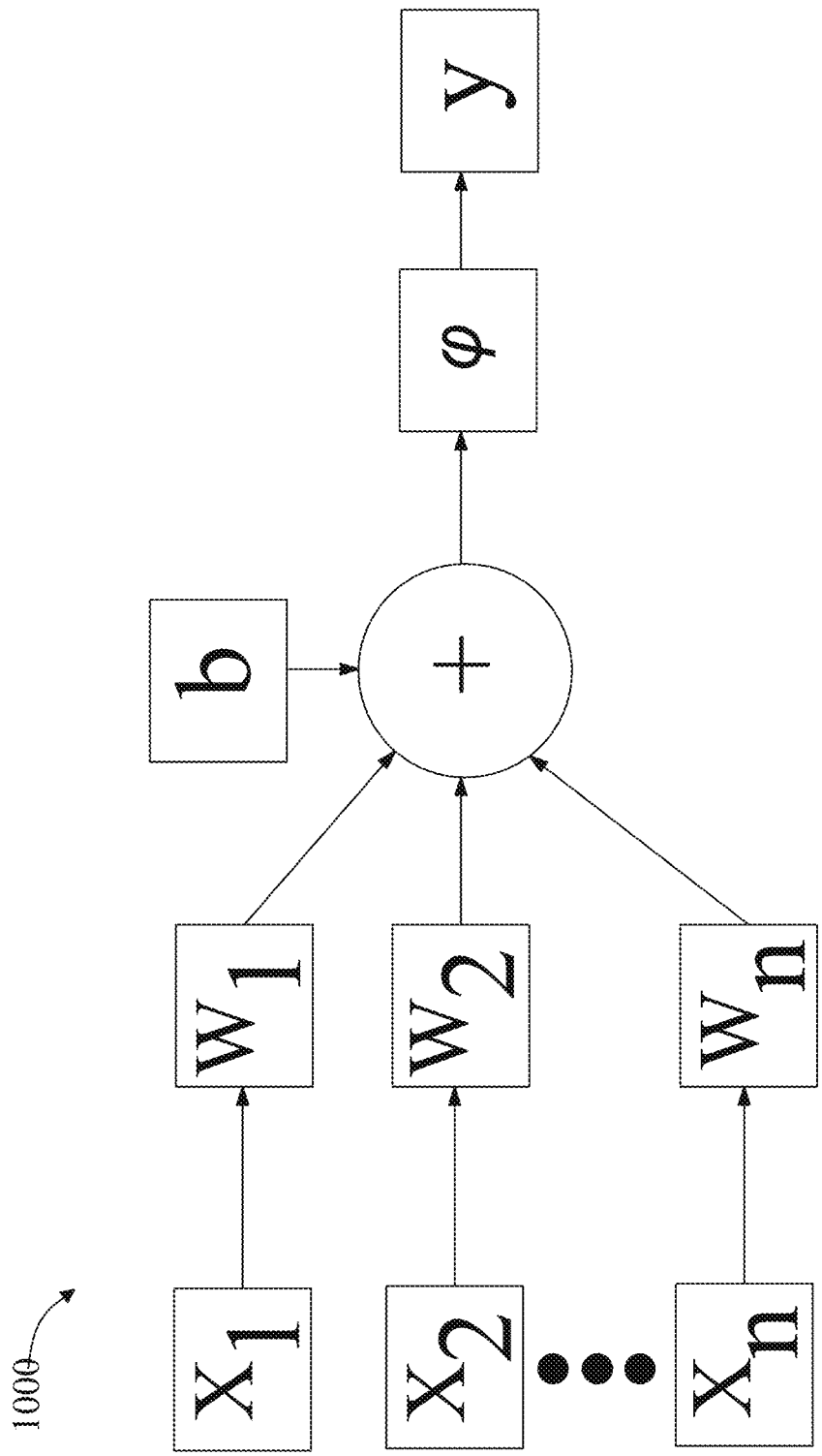
FIG. 10 is a schematic diagram of an exemplary embodiment of a node of a neural network.

Referring now to FIG. 10, an exemplary embodiment of a node 1000 of a neural network is illustrated. A node 1000 may include, without limitation, a plurality of inputs $x_i$ that may receive numerical values from inputs to a neural network containing the node and/or from other nodes. Node 1000 may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 10, a neural network may receive biofeedback 124 as inputs and output on or more of a display parameter. Alternatively or additionally in some cases, a neural network may receive biofeedback 124 data as inputs and output confidence metric representing a probability of classification to a predetermined class, for instance user state 136, according to weights $w_i$ that are derived using machine-learning processes as described in this disclosure.

Referring again to FIG. 1, in some embodiments, computing device 104 may be configured to modify a training set in response to a biofeedback signal 132 correlated to a display parameter; where the display parameter may represent an actual known occurrence that is related to a user state 136. For example, computing device 104 may, in some cases, retrain a machine-learning model, for instance display machine-learning model, using a biofeedback signal 132 correlated to a user state 136. In some embodiments, computing device 104 may be configured to classify at least one of a user state 136 and a display parameter and determine a confidence metric. For example, in some exemplary embodiments confidence metric may be a floating-point number within a prescribed range, such as without limitation 0 to 1, with each end of the prescribed range representing an extreme representation, such as without limitation substantially no confidence and substantially absolute confidence, respectively. In some cases, confidence output may represent a relationship between a result of filtering and/or classifying a user state 136. Confidence metric may be determined by one more comparisons algorithm, such as without limitation a fuzzy set comparison. For example, in some exemplary embodiments a fuzzy set comparison may be employed to compare a probabilistic outcome with a membership function derived to represent at least a threshold used for classification.

Figure 11:
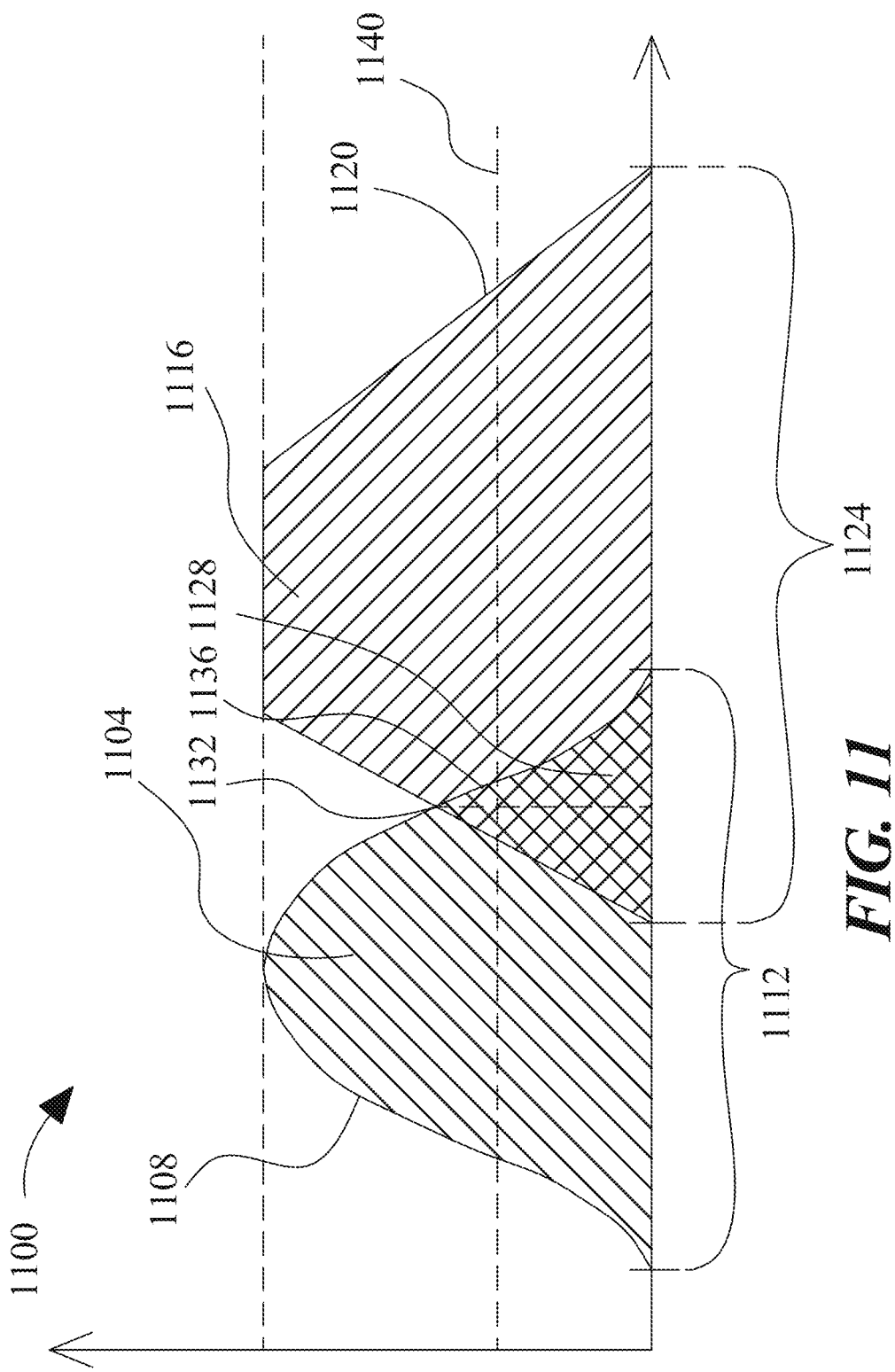
FIG. 11 is a graph representing an exemplary embodiment of a fuzzy set comparison.

Referring to FIG. 11, an exemplary embodiment of fuzzy set comparison 1100 is illustrated. A first fuzzy set 1104 may be represented, without limitation, according to a first membership function 1108 representing a probability that an input falling on a first range of values 1112 is a member of the first fuzzy set 1104, where the first membership function 1108 has values on a range of probabilities such as without limitation the interval [0,1], and an area beneath the first membership function 1108 may represent a set of values within first fuzzy set 1104. Although first range of values 1112 is illustrated for clarity in this exemplary depiction as a range on a single number line or axis, first range of values 1112 may be defined on two or more dimensions, representing, for instance, a Cartesian product between a plurality of ranges, curves, axes, spaces, dimensions, or the like. First membership function 1108 may include any suitable function mapping first range 1112 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 11, first fuzzy set 1104 may represent any value or combination of values as described above, including output from one or more machine-learning models and biofeedback signal 132s from sensor 128, a predetermined class, such as without limitation a user state 136 (e.g., attentive, inattentive, honest, dishonest, and the like). A second fuzzy set 1116, which may represent any value which may be represented by first fuzzy set 1104, may be defined by a second membership function 1120 on a second range 1124; second range 1124 may be identical and/or overlap with first range 1112 and/or may be combined with first range via Cartesian product or the like to generate a mapping permitting evaluation overlap of first fuzzy set 1104 and second fuzzy set 1116. Where first fuzzy set 1104 and second fuzzy set 1116 have a region 1128 that overlaps, first membership function 1108 and second membership function 1120 may intersect at a point 1132 representing a probability, as defined on probability interval, of a match between first fuzzy set 1104 and second fuzzy set 1116. Alternatively or additionally, a single value of first and/or second fuzzy set may be located at a locus 1136 on first range 1112 and/or second range 1124, where a probability of membership may be taken by evaluation of first membership function 1108 and/or second membership function 4110 at that range point. A probability at 1128 and/or 1132 may be compared to a threshold 1140 to determine whether a positive match is indicated. Threshold 1140 may, in a non-limiting example, represent a degree of match between first fuzzy set 1104 and second fuzzy set 1116, and/or single values therein with each other or with either set, which is sufficient for purposes of the matching process; for instance, threshold may indicate a sufficient degree of overlap between an output from one or more machine-learning models and/or a biofeedback signal 132 and a predetermined class, such as without limitation a user state 136, for combination to occur as described above. Alternatively or additionally, each threshold may be tuned by a machine-learning and/or statistical process, for instance and without limitation as described in further detail below.

Further referring to FIG. 11, in an embodiment, a degree of match between fuzzy sets may be used to classify a biofeedback signal 132 with a user state 136. For instance, if a biofeedback signal 132 has a fuzzy set matching a user state 136 fuzzy set by having a degree of overlap exceeding a threshold, computing device 104 may classify the biofeedback signal 132 as belonging to the user state 136. Where multiple fuzzy matches are performed, degrees of match for each respective fuzzy set may be computed and aggregated through, for instance, addition, averaging, or the like, to determine an overall degree of match.

Still referring to FIG. 11, in an embodiment, a biofeedback signal 132 may be compared to multiple user state 136 fuzzy sets. For instance, biofeedback signal 132 may be represented by a fuzzy set that is compared to each of the multiple user state 136 fuzzy sets; and a degree of overlap exceeding a threshold between the biofeedback signal 132 fuzzy set and any of the multiple user state 136 fuzzy sets may cause computing device 104 to classify the biofeedback signal 132 as belonging to a user state 136. For instance, in one embodiment there may be two user state 136 fuzzy sets, representing respectively an honest state and a dishonest state. Honest state may have an Honest state fuzzy set; dishonest state may have a dishonest state fuzzy set; and biofeedback signal 132 may have a biofeedback 124 fuzzy set. Computing device 104, for example, may compare a biofeedback 124 fuzzy set with each of honest state fuzzy set and dishonest state fuzzy set, as described above, and classify a biofeedback signal 132 to either, both, or neither of honest state nor dishonest state. Machine-learning methods as described throughout may, in a non-limiting example, generate coefficients used in fuzzy set equations as described above, such as without limitation x, c, and σ of a Gaussian set as described above, as outputs of machine-learning methods. Likewise, biofeedback signal 132 may be used indirectly to determine a fuzzy set, as biofeedback 124 fuzzy set may be derived from outputs of one or more machine-learning models that take the biofeedback signal 132 directly or indirectly as inputs.

Figure 12:
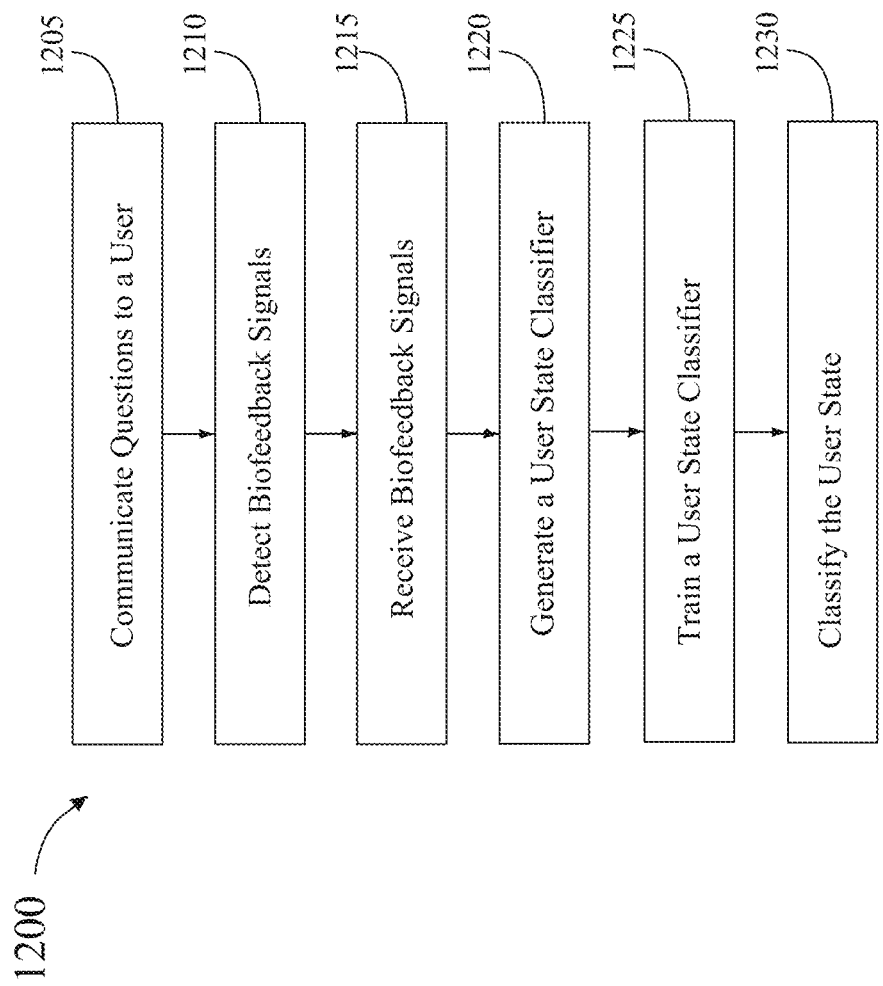
FIG. 12 is a flow diagram of an exemplary method of individualized polygraph testing.

Referring now to FIG. 12, is a flow diagram of exemplary method 1200 individualized polygraph testing is illustrated. At step 1205, method 1200 includes communicating, by at least an interface, questions to the user, as implemented and with reference to FIGS. 1-11. At least an interface may include an audio-visual interface. At step 1210, method 1200 includes detecting, by at least a sensor, biofeedback signals as a function of a biofeedback of a user, wherein the biofeedback is associated with at least an answer to at least a question, as implemented and with reference to FIGS. 1-11. The at least a sensor may include an optical sensor. The at least a sensor may include a cutaneous sensor. At step 1215, method 1200 includes receiving, by a computing device, the biofeedback signals, as implemented and with reference to FIGS. 1-11. Biofeedback signals may include at least a circulatory parameter. The circulatory parameter may include a pulse rate. Classifying the at least a biofeedback signal may further include receiving the at least an answer to the at least a question from the user as input into the user state classifier. At step 1220, method 1200 includes generating, by the computing device, a user state classifier as a function of a user state machine-learning algorithm, as implemented and with reference to FIGS. 1-11. At step 1225, method 1200 includes training, by the computing device, the user state classifier as a function of a user state training set, wherein the user state training set comprises biofeedback signals correlated to answers of known veracity, as implemented and with reference to FIGS. 1-11. At step 1230, method 1200 includes classifying, by the computing device, the user state as a function of the user state classifier and at least a biofeedback signal. as implemented and with reference to FIGS. 1-11. The user state may include one of honest, dishonest, or indeterminate. The user state may be associated with a user's present confidence. The computing device may be further configured to generate a confidence metric associated with the user state Referring again to FIG. 1, apparatus 100 may be used in any number of applications, many non-limiting examples have been provided throughout this disclosure. In some embodiments, apparatus 100 may be used to provide a practical improvement to online classes. Online classes have seen an increase in popularity and use since the Covid pandemic, forcing most people to isolate. Students and teachers have been forced to learn and teach remotely, engaging with one another by way of computer, a display, and audio. As a result of this, many subtle cues between teachers and students have been lost. A good teacher (or presenter generally) will look to her students (or audience generally) for non-verbal signs of engagement. This sign can include a raised eyebrow at a contentious moment of the course, a laugh at a presenter's joke, and the like. Many of these interpersonal feedbacks are obfuscated by current online teaching platforms. As a result of this, ambiguity arises over how much of a class students are receiving, and many teachers have found teaching remotely more difficult and less rewarding. In some exemplary embodiments, apparatus 100 is used to improve upon this difficulty and provide feedback characterizing quality of communication with one or more students 116 to a teacher. This feedback, in some cases, may be considered a metric of communication. In some cases, metric of communication may be presented to teacher through any means, including color coding, gauges, and the like. In some cases, a teacher will be presented with a metric of communication for each student with a color code (e.g., red representing poor communication, yellow representing moderate communication, and green representing good communication) with or without a numerical value. The teacher may then detect from this which student are engaged, and which are not. In some cases, the teacher may be presented with an aggregated metric of communication for a group of students. For example, an aggregated metric of communication may communicate how well an entire class is receiving instruction from the teacher.

In another exemplary embodiment, apparatus 100 may be used with real-time question, for example a live presenter (no display). In this cases apparatus 100 may adjust audio of presentation.

In yet another exemplary embodiment, apparatus 100 may be used to identify a user 120. For example, in some cases, apparatus 100 may detect and/or confirm an identity of an individual user 120. Apparatus 100 may determine and/or confirm an identity of an individual user 120 by using at least a biofeedback 124 and/or a user state 136. In some cases, at least a biofeedback 124 may be used as an input to at least a machine-learning process (e.g., machine-learning model) that is configured to identify an individual user 120 as a function of at least a biofeedback 124 (e.g., image of the user 120) and or user state 136. In some cases, machine-learning models may be trained using training data that includes inputs including representative biofeedback 124s correlated with individual user 120 identities. A user 120-identifying machine-learning process may include any machine-learning process described in this disclosure, including without limitation supervised machine-learning processes, unsupervised machine-learning processes, and classifiers. In some exemplary applications, apparatus 100 may identify an individual user 120 prior to, during, and/or after completion of question delivery. Apparatus 100 may continuously and/or periodically identify an individual user 120. Apparatus 100 may periodically identify an individual user 120 in order to maintain proof that the individual has not changed and is the individual user 120 for which the question is intended. In one application, apparatus 100 may be used to ensure that an individual user 120 is the one receiving intended question during an examination, such as without limitation a remote scholastic aptitude test (SAT). As described throughout this disclosure and continuing with the SAT exemplary application, the apparatus 100 may confirm not only a user's identity, but also her level of honesty, attention and/or engagement during the test. Although described in reference to an SAT test, system's 100 ability to continuously detect and/or confirm the identity of a user 120 may be useful in other applications to ensure that sensitive question is being delivered only to an intended audience.

In still another exemplary embodiment, apparatus 100 may be used in conjunction with one or more other systems capable of determining and/or quantifying physical performance. For example, a user 120 may be engaged in a physically strenuous activity (in addition to or instead of a mentally challenging activity). Physically strenuous activity may have certain metrics of performance, which are measured. For instance, where a physically strenuous activity includes a treadmill, confidence metrics may include rate of the treadmill, incline of the treadmill, and the like. Alternatively or additionally, where physically strenuous activity includes a weight, confidence metric may include number of repetitions, number of sets, mass of the weight, and the like. In some cases, apparatus 100 may take as input a confidence metric of a physically strenuous activity. Alternatively or additionally, a confidence metric of a physically strenuous activity may include amount of time on-duty or in a state of wakefulness. Apparatus 100 may determine correlations and/or predictions based upon one or more of confidence metrics, biofeedback 124, user state 136, display parameters, for example by using any machine-learning process described above in this disclosure, for example with reference to FIGS. 1-11.

It is to be noted that any one or more of the aspects and embodiments described herein may be conveniently implemented using one or more machines (e.g., one or more computing devices that are utilized as a user 120 computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
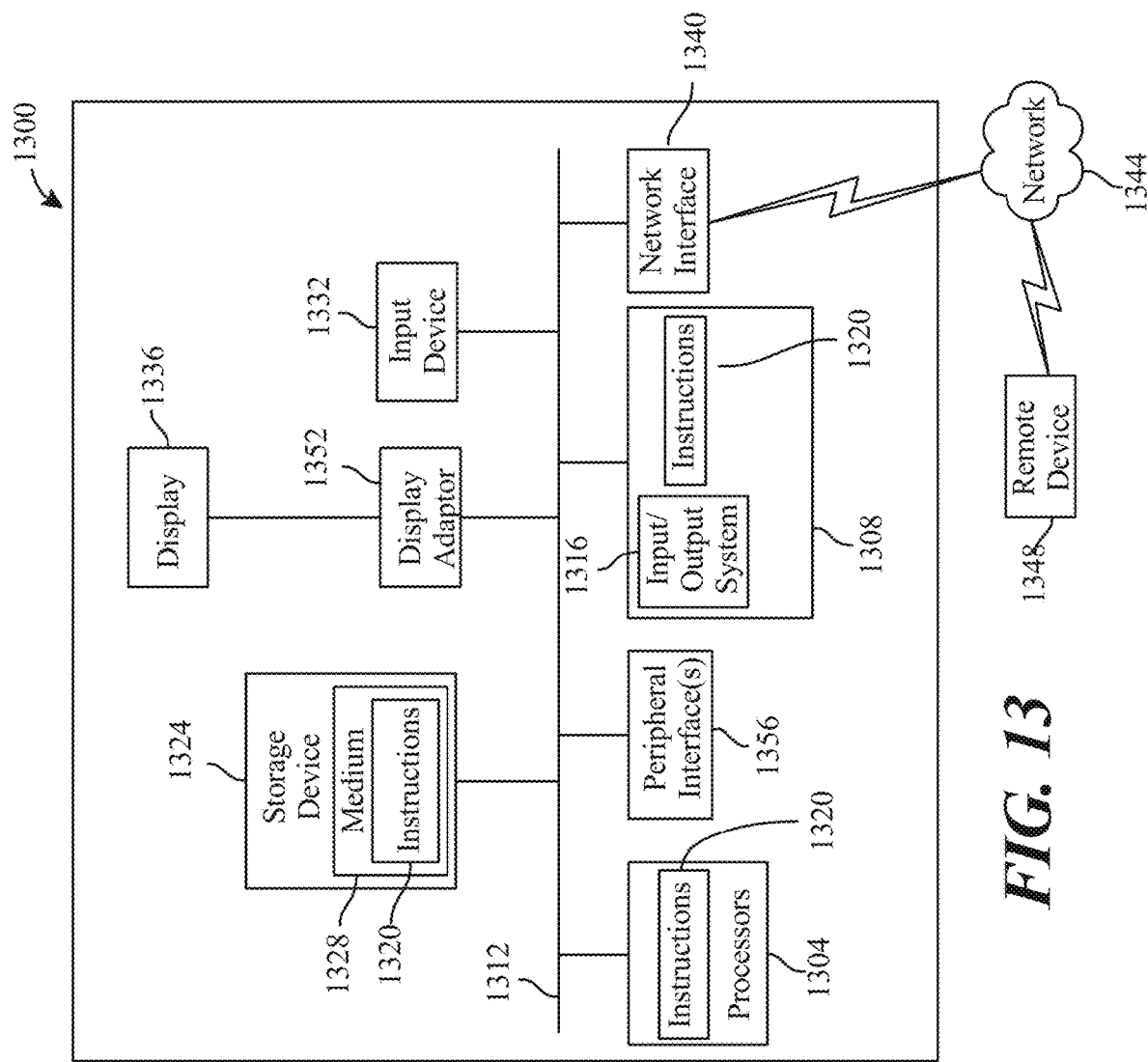
FIG. 13 is a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Processor 1304 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1304 may be organized according to Von Neumann and/or Harvard architecture as a non-limiting example. Processor 1304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIREWIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for individualized polygraph testing, the apparatus comprising:
   at least an interface configured to communicate questions to a user;
   at least a sensor configured to detect biofeedback signals as a function of a biofeedback of the user, wherein the biofeedback is associated with at least an answer to at least a question; and
   at least a computing device comprising:
      at least a processor; and
      a memory communicatively connected to the at least a processor, the memory containing instructions configuring the at least a processor to:
         receive the biofeedback signals;
         generate a user state classifier as a function of a user state machine-learning algorithm;
         train the user state classifier as a function of a user state training set, wherein the user state training set comprises biofeedback signals correlated to answers of known veracity;
         classify at least a biofeedback signal of the biofeedback signals to a user state as a function of the user state classifier;
         generate a confidence metric based on the user state; and
         control a speed of presentation of a plurality of questions including the at least a question in response to the biofeedback signal of the biofeedback signals, wherein the speed of presentation is continuously varied in proportion to the confidence metric.

2. The apparatus of claim 1, wherein the biofeedback signals comprise at least a circulatory parameter.

3. The apparatus of claim 1, wherein the speed of presentation is discretely varied in proportion to the confidence metric, the confidence metric generated according to the biofeedback signal; and
   wherein the memory contains further instructions configuring the at least a processor to receive the at least an answer to the at least a question from the user.

4. The apparatus of claim 1, wherein the at least an interface comprises an audio-visual interface.

5. The apparatus of claim 1, wherein the at least a sensor comprises an optical sensor.

6. The apparatus of claim 1, wherein the at least a sensor comprises a cutaneous sensor.

7. The apparatus of claim 1, wherein the circulatory parameter comprises a pulse rate.

8. The apparatus of claim 1, wherein the user state comprises a state chosen from a group consisting of honest, dishonest, and indeterminate.

9. The apparatus of claim 1, wherein the user state is associated with a user present confidence.

10. A method for individualized polygraph testing, the method comprising:
    communicating, by at least an interface, questions to a user;
    detecting, by at least a sensor, biofeedback signals as a function of a biofeedback of the user, wherein the biofeedback is associated with at least an answer to at least a question; and
    receiving, by a computing device, the biofeedback signals;
    generating, by the computing device, a user state classifier as a function of a user state machine-learning algorithm;
    training, by the computing device, the user state classifier as a function of a user state training set, wherein the user state training set comprises biofeedback signals correlated to answers of known veracity;
    classifying, by the computing device, at least a biofeedback signal of the biofeedback signals to a user state as a function of the user state classifier;
    generating, by the computing device, a confidence metric based on the user state; and
    controlling, by the computing device, a speed of presentation of a plurality of questions including the at least a question in response to the biofeedback signal of the biofeedback signals, wherein the speed of presentation is continuously varied in proportion to the confidence metric.

11. The method of claim 10, wherein the biofeedback signals comprise at least a circulatory parameter.

12. The method of claim 10, further comprising receiving, by the computing device, the at least an answer to the at least a question from the user, and wherein the speed of presentation is discretely varied in proportion to the confidence metric, the confidence metric generated according to the biofeedback signal.

13. The method of claim 10, wherein the at least an interface comprises an audio-visual interface.

14. The method of claim 10, wherein the at least a sensor comprises an optical sensor.

15. The method of claim 10, wherein the at least a sensor comprises a cutaneous sensor.

16. The method of claim 10, wherein the circulatory parameter comprises a pulse rate.

17. The method of claim 10, wherein the user state comprises a state chosen from a group consisting of honest, dishonest, and indeterminate.

18. The method of claim 10, wherein the user state is associated with a user present confidence.

* * * * *